(12) United States Patent
Yu et al.

(10) Patent No.: US 11,330,913 B2
(45) Date of Patent: May 17, 2022

(54) METHOD FOR OPERATING SMART MATTRESS SYSTEM ENABLING ALARM CONTROL

(71) Applicant: IOBED INC., Goyang-si (KR)

(72) Inventors: Young Jun Yu, Anyang-si (KR); Dong Hun Lee, Cheonan-si (KR); Keon Yong Lee, Goyang-si (KR); Dong Wook Shin, Paju-si (KR); Seung Mo Kim, Seoul (KR)

(73) Assignee: IOBED INC., Paju-si (KR)

( * ) Notice: Subject to any disclaimer, the term of this patent is extended or adjusted under 35 U.S.C. 154(b) by 110 days.

(21) Appl. No.: 16/767,599

(22) PCT Filed: Dec. 27, 2017

(86) PCT No.: PCT/KR2017/015566
§ 371 (c)(1),
(2) Date: May 28, 2020

(87) PCT Pub. No.: WO2019/107661
PCT Pub. Date: Jun. 6, 2019

(65) Prior Publication Data
US 2020/0405072 A1    Dec. 31, 2020

(30) Foreign Application Priority Data

Nov. 28, 2017  (KR) .................. 10-2017-0160945

(51) Int. Cl.
*A47C 27/08*    (2006.01)
*A47C 31/12*    (2006.01)
(Continued)

(52) U.S. Cl.
CPC .......... *A47C 27/083* (2013.01); *A47C 31/123* (2013.01); *A47G 9/1027* (2013.01);
(Continued)

(58) Field of Classification Search
CPC ... A47C 27/083; A47C 31/123; A47C 31/008; A47C 27/082; A47C 27/10;
(Continued)

(56) References Cited

U.S. PATENT DOCUMENTS

| 6,928,031 B1 * | 8/2005 | Kanevsky | .............. G16H 40/67 |
|---|---|---|---|
| | | | 368/12 |
| 2004/0177449 A1 * | 9/2004 | Wong | ..................... A47C 27/10 |
| | | | 5/713 |

FOREIGN PATENT DOCUMENTS

| JP | 2001-231864 A | | 8/2001 | |
|---|---|---|---|---|
| JP | 2001231864 | * | 8/2001 | ............ A61M 21/00 |

(Continued)

OTHER PUBLICATIONS

"Range." Merriam-Webster, Merriam-Webster, www.merriam-webster.com/dictionary/range.*

(Continued)

*Primary Examiner* — David R Hare
*Assistant Examiner* — Madison Emanski
(74) *Attorney, Agent, or Firm* — Revolution IP, PLLC

(57) ABSTRACT

The present invention relates to a method of operating a smart mattress system enabling alarm control, wherein a user is allowed to transition to a light sleep state before an alarm time set by the user. Furthermore, an air mattress and an air pillow interlock with a user terminal so that the user can easily control the air mattress and the air pillow.

15 Claims, 25 Drawing Sheets

(51) Int. Cl.
    *A47G 9/10*           (2006.01)
    *A47C 31/00*         (2006.01)
    *A61H 1/00*          (2006.01)
    *G04F 10/00*         (2006.01)

(52) U.S. Cl.
    CPC ............ *A47C 31/008* (2013.01); *A61H 1/001* (2013.01); *A61H 2201/0146* (2013.01); *G04F 10/00* (2013.01)

(58) Field of Classification Search
    CPC ................. A47G 9/1027; A61H 1/001; A61H 2201/0146; G04F 10/00; A61B 5/4812; A61M 2021/0083
    See application file for complete search history.

(56) References Cited

FOREIGN PATENT DOCUMENTS

| | | |
|---|---|---|
| JP | 2006-519648 A | 8/2006 |
| JP | 2014-064692 A | 4/2014 |
| JP | 2016-028663 A | 3/2016 |
| KR | 10-2003-0061267 A | 7/2003 |
| KR | 10-2010-0022706 A | 3/2010 |

OTHER PUBLICATIONS

International Search Report for PCT/KR2017/015566 dated Sep. 10, 2018 from Korean Intellectual Property Office.

\* cited by examiner

[FIG. 1]
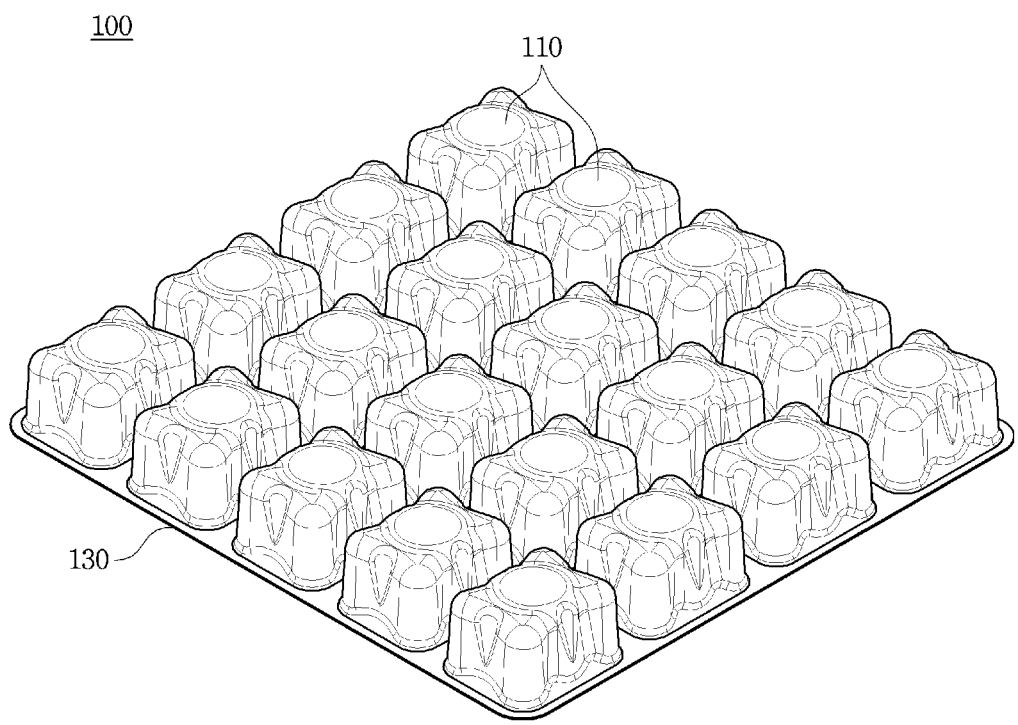

[FIG. 2]
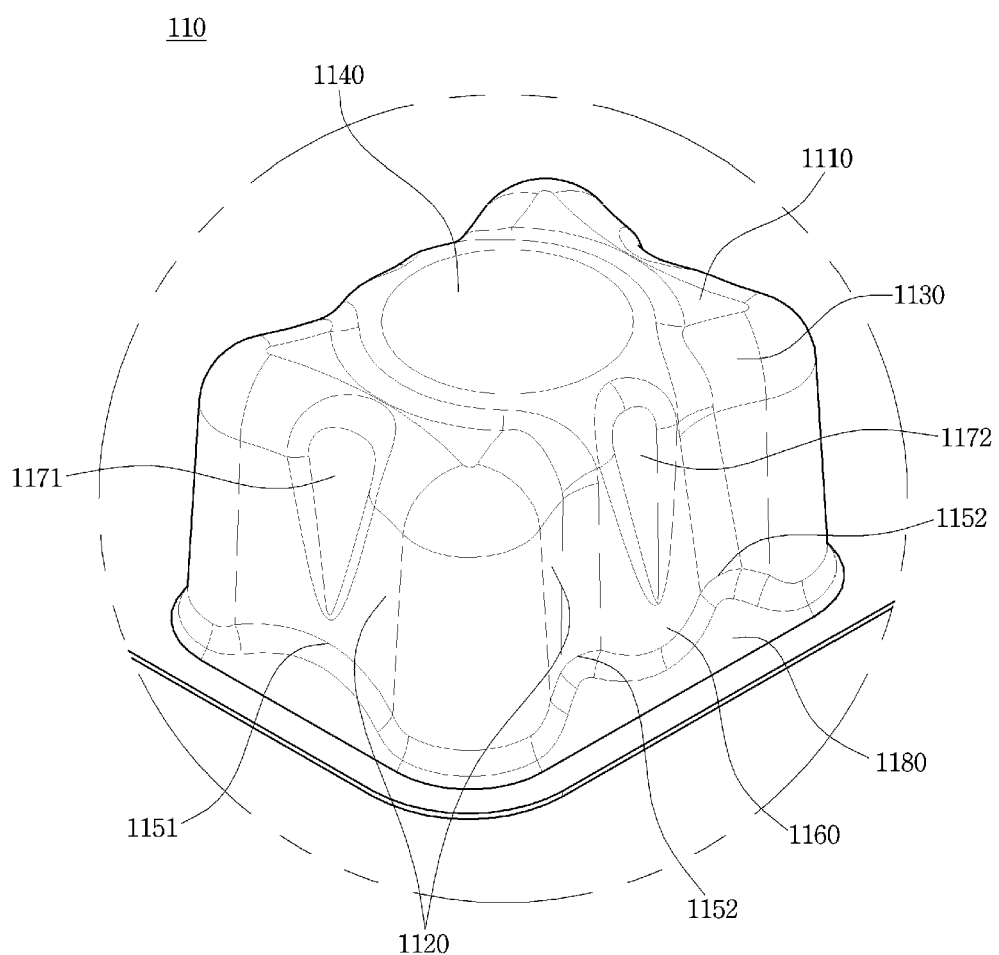

[FIG. 3]
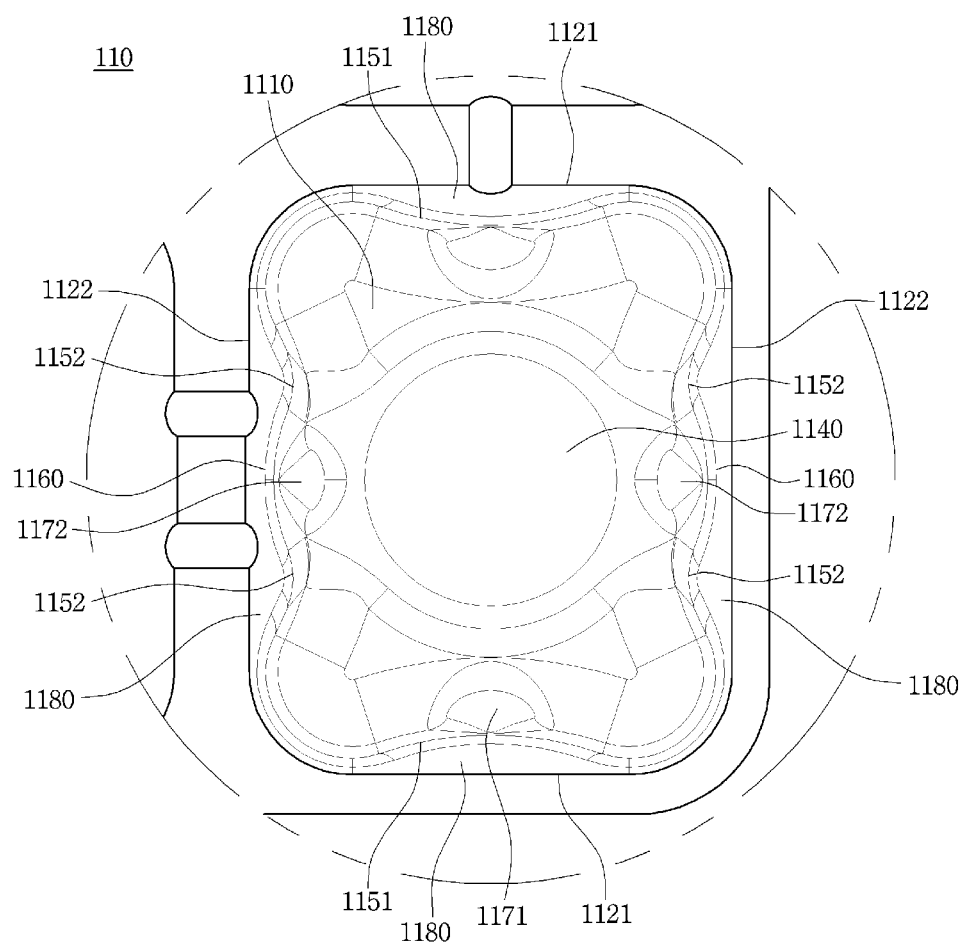

[FIG. 4]
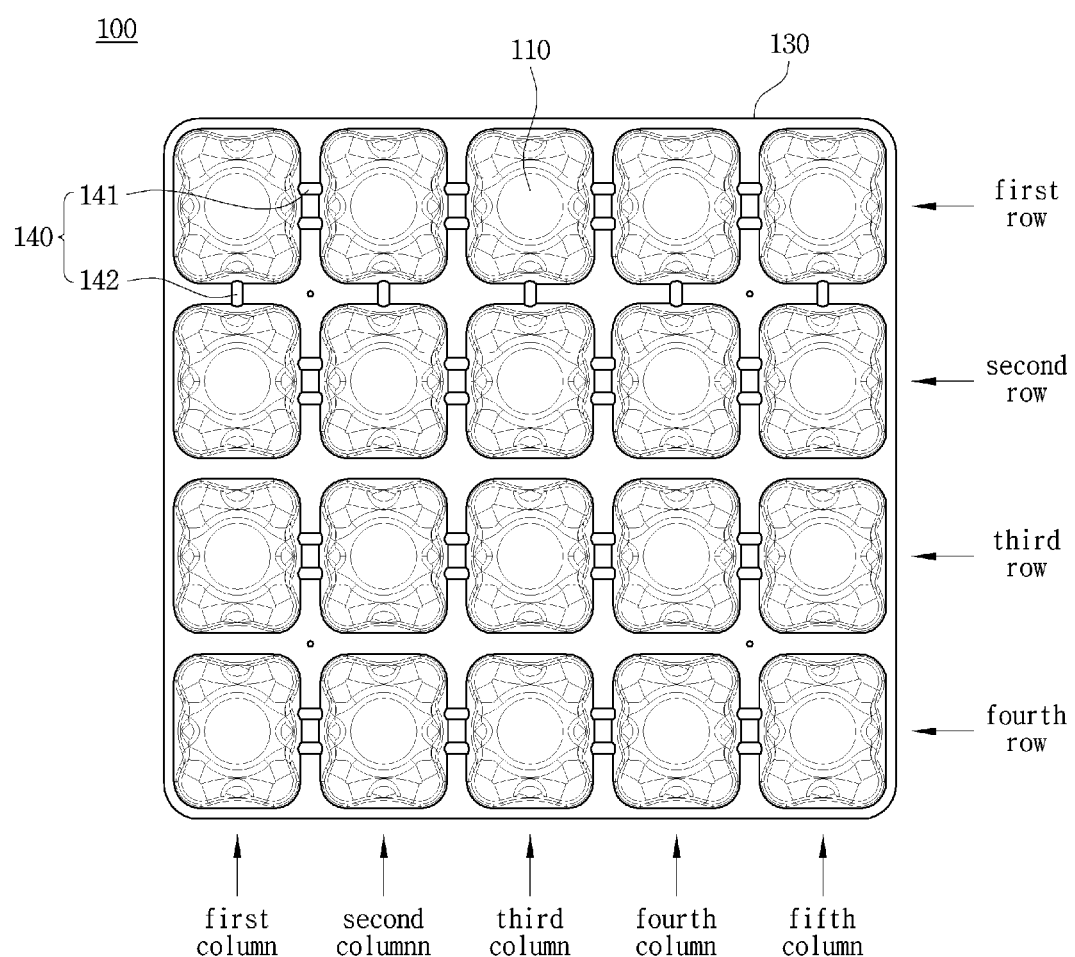

[FIG. 5]
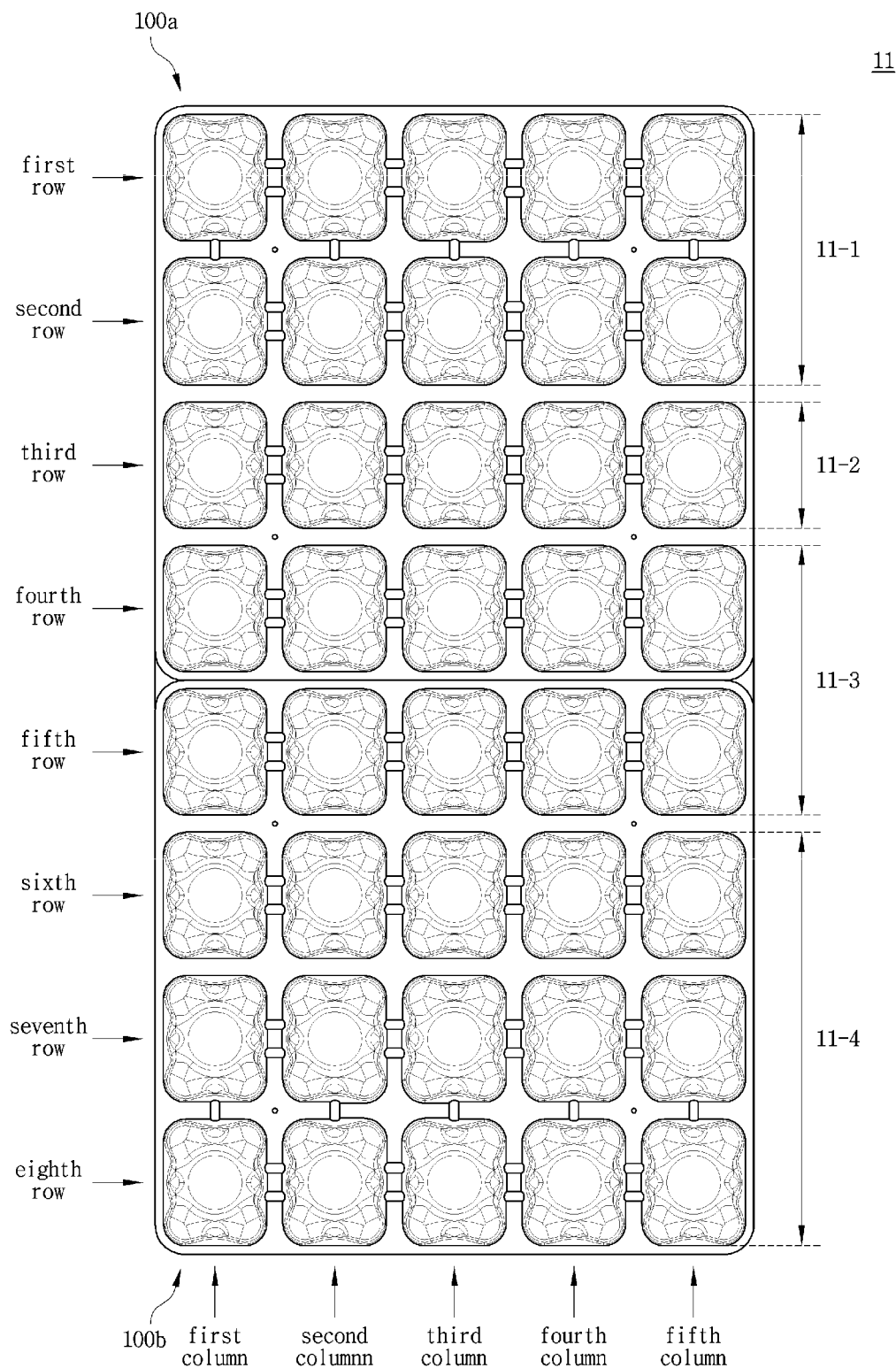

[FIG. 6]
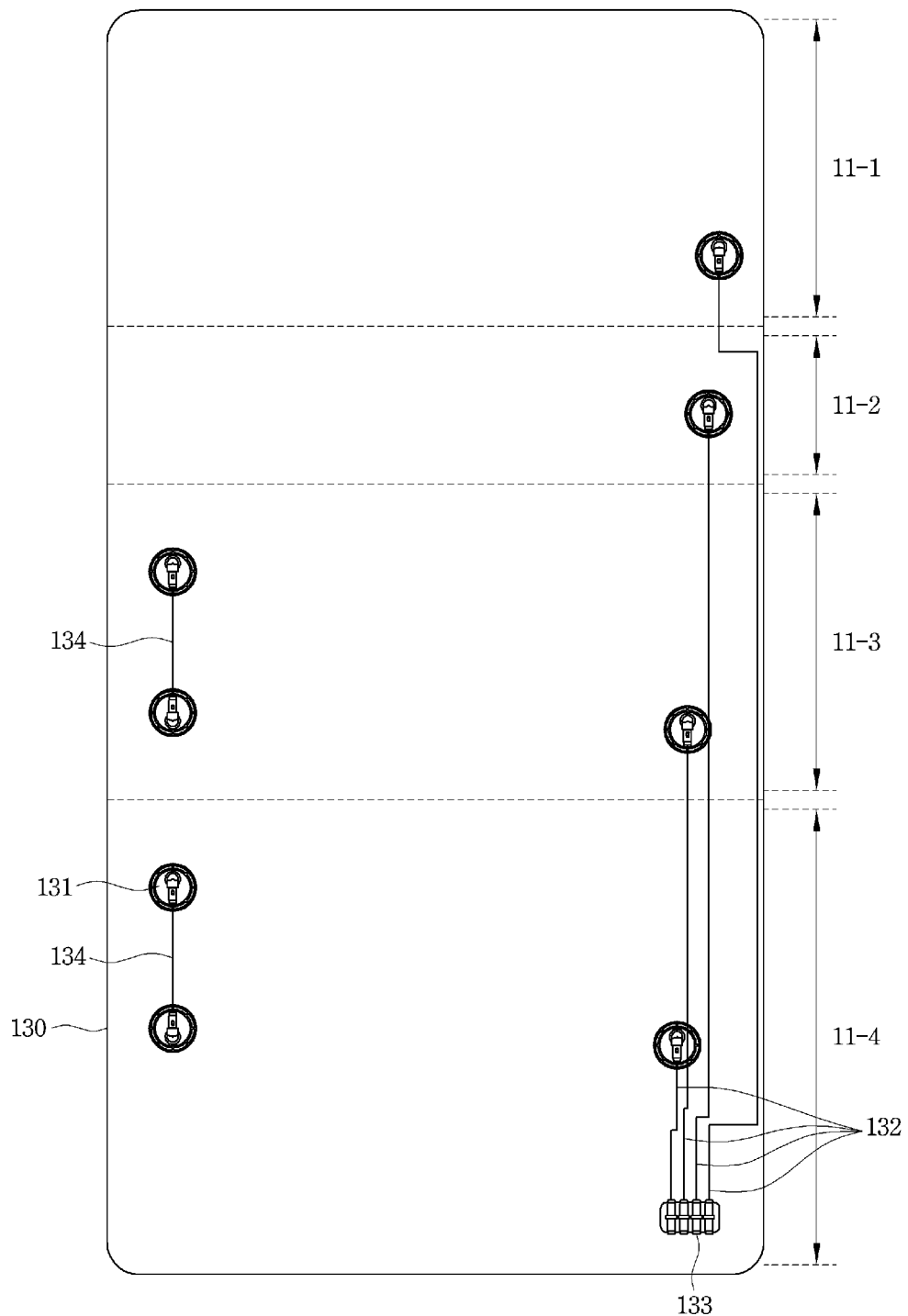

[FIG. 7]
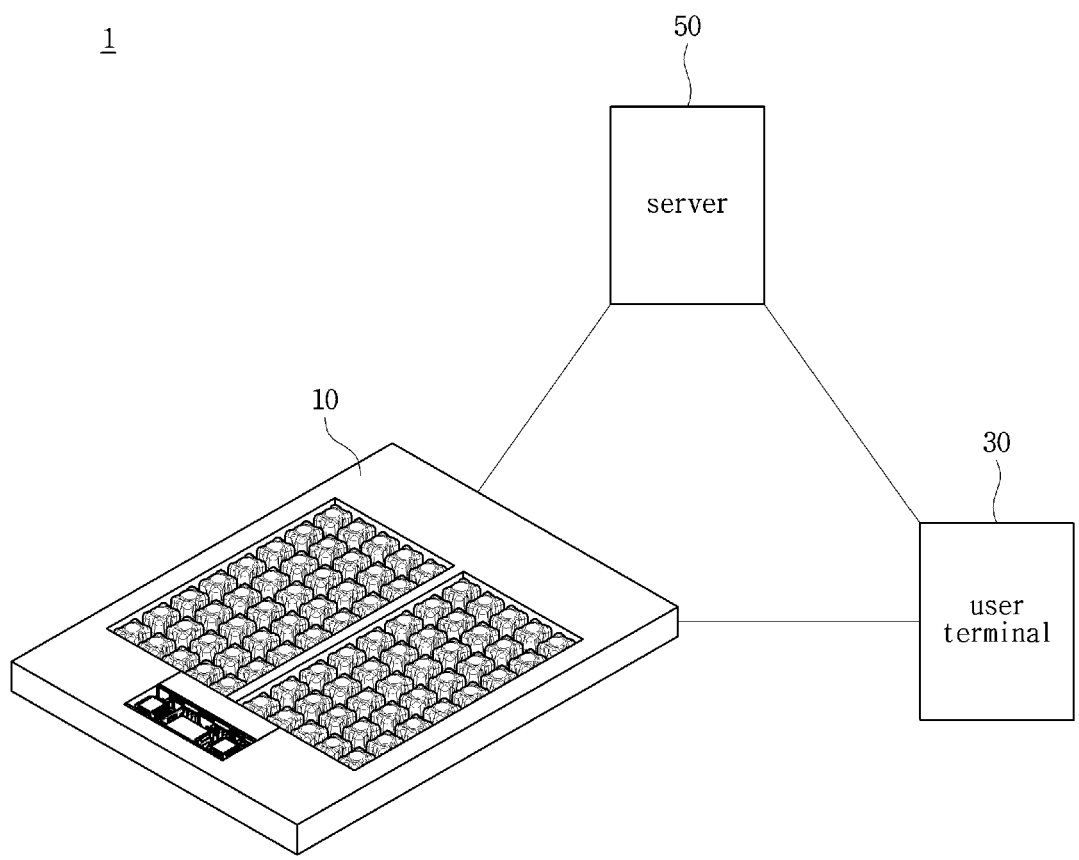

[FIG. 8]
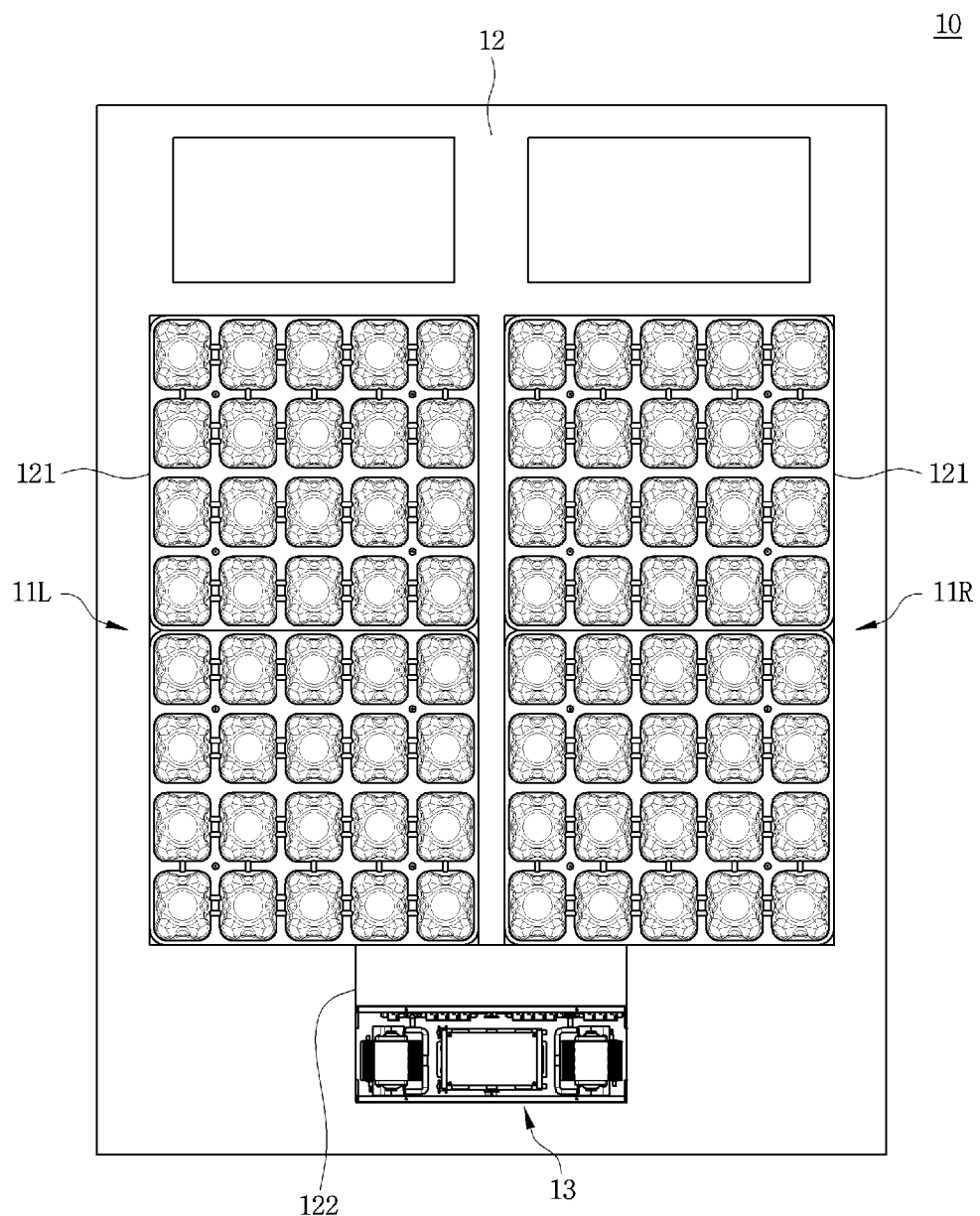

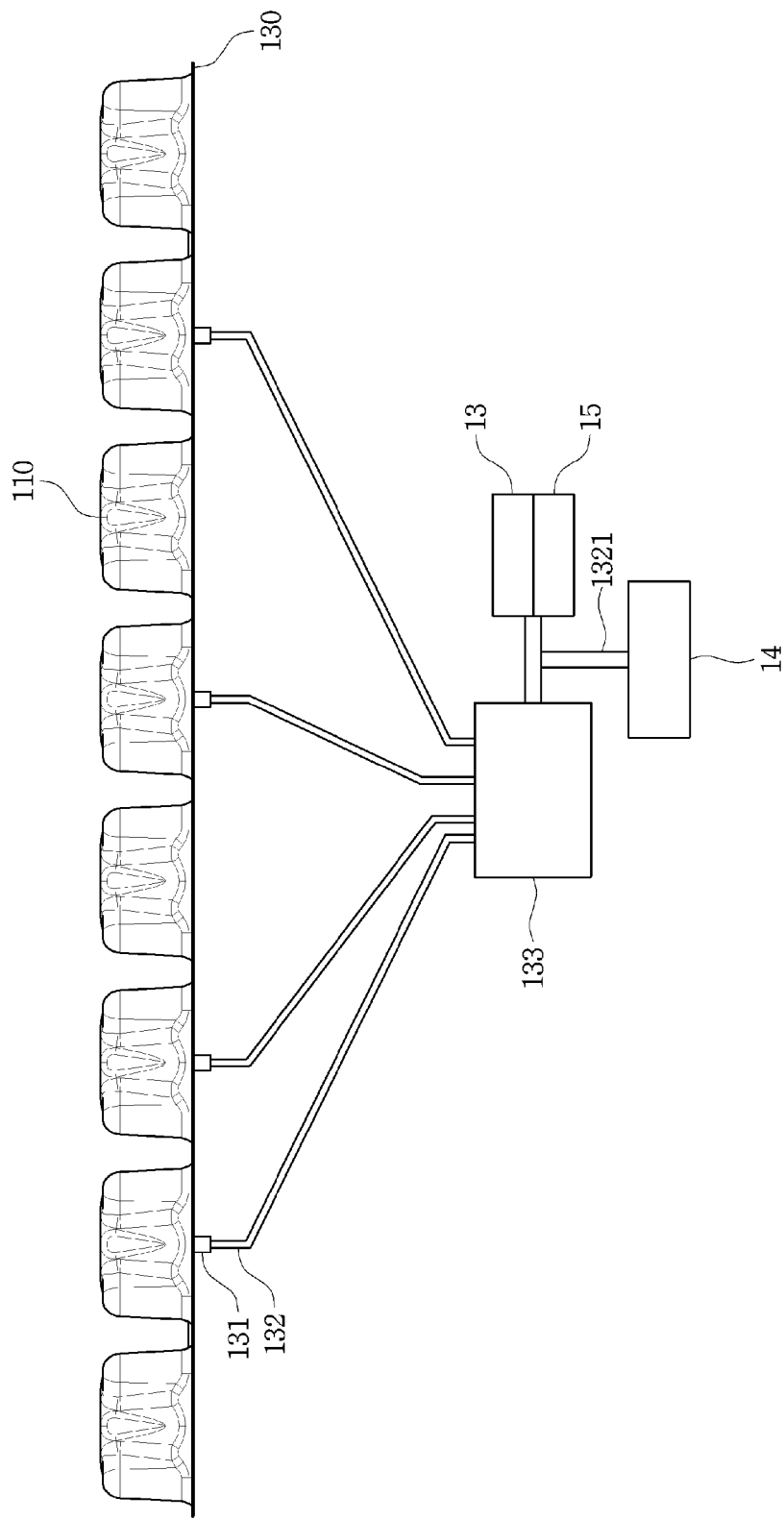

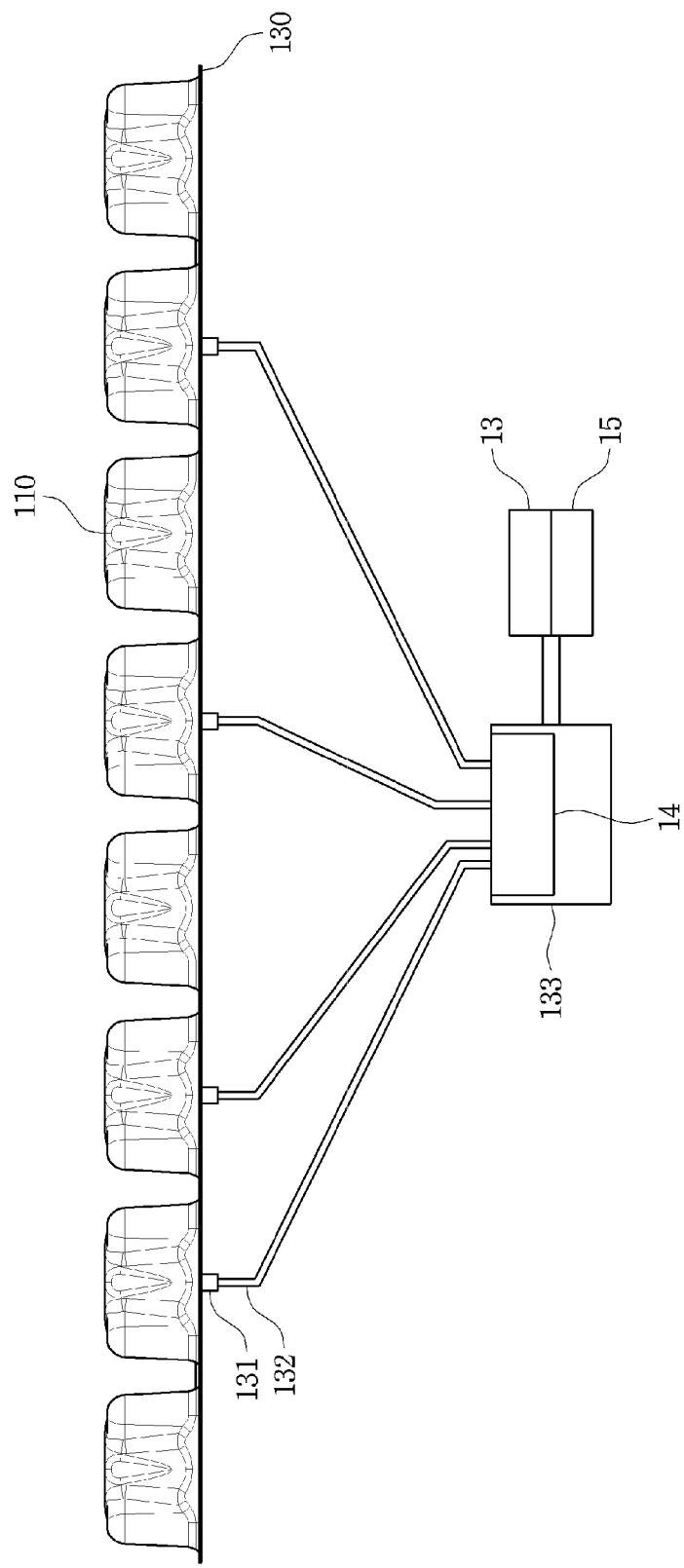
[FIG. 10]

[FIG. 11]
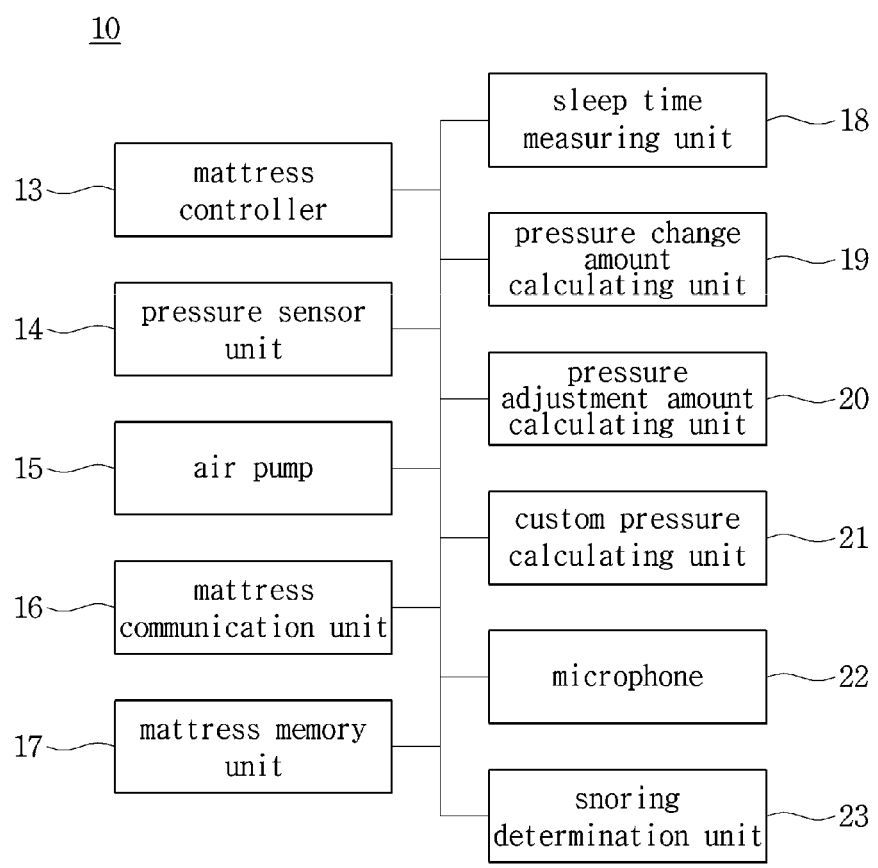

[FIG. 12]
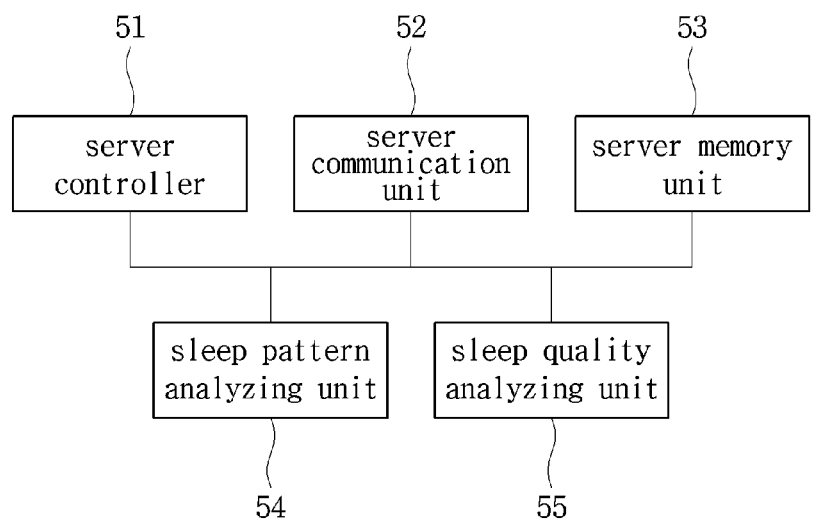

[FIG. 13A]
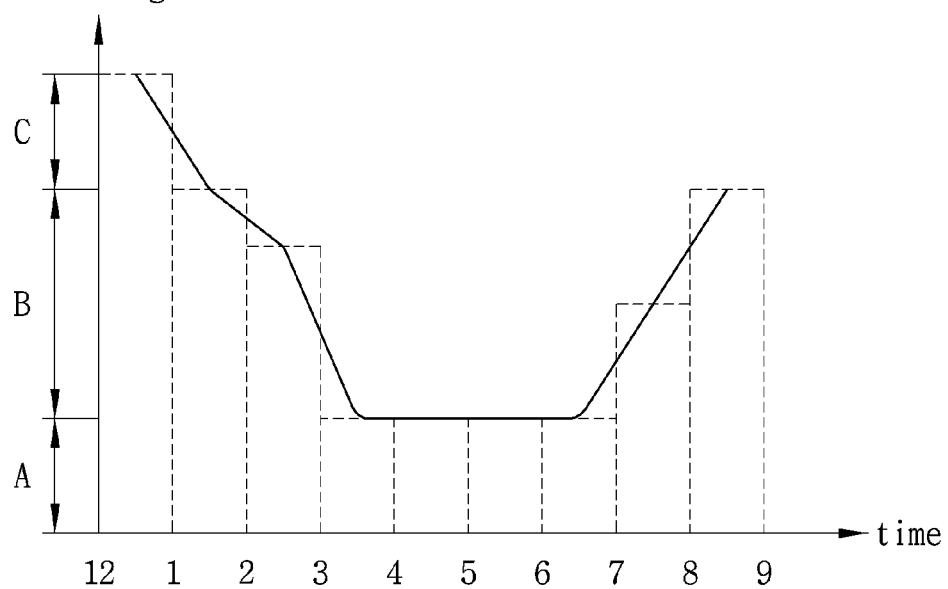

[FIG. 13B]

$$\frac{(a \times time)+(b \times time)+(c \times time)}{time} = \frac{(a \times 4)+(b \times 2)+(c \times 3)}{9}$$

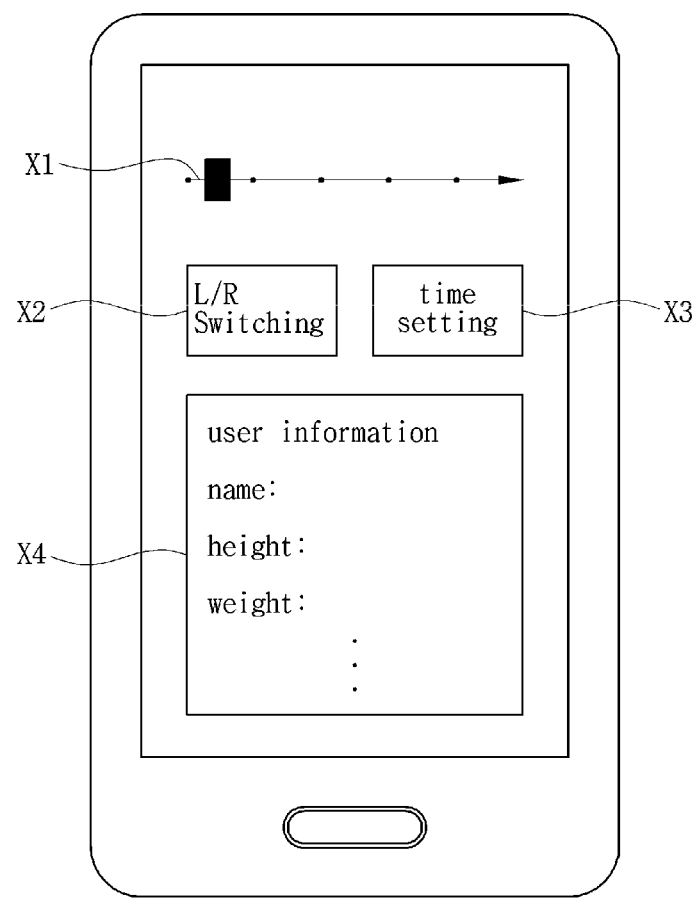
[FIG. 14A]

[FIG. 14B]
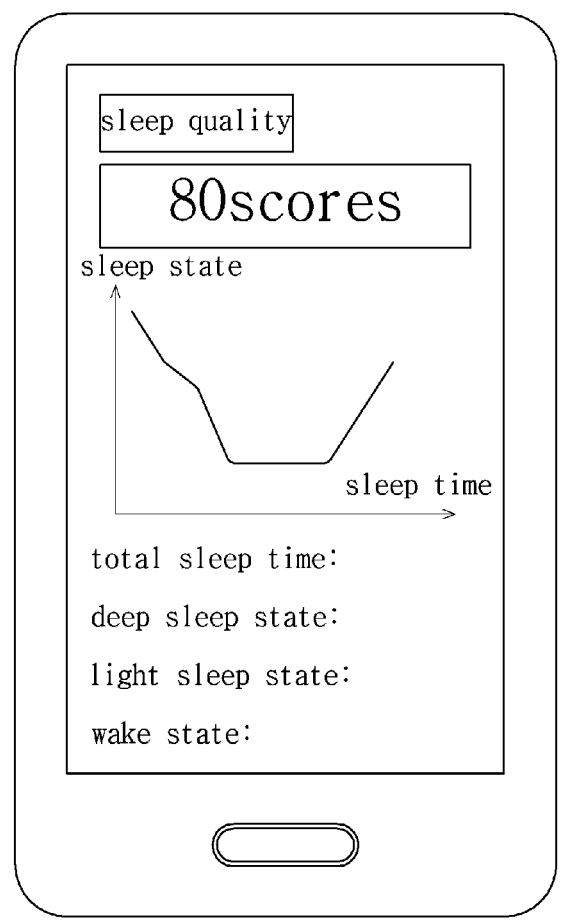

[FIG. 14C]
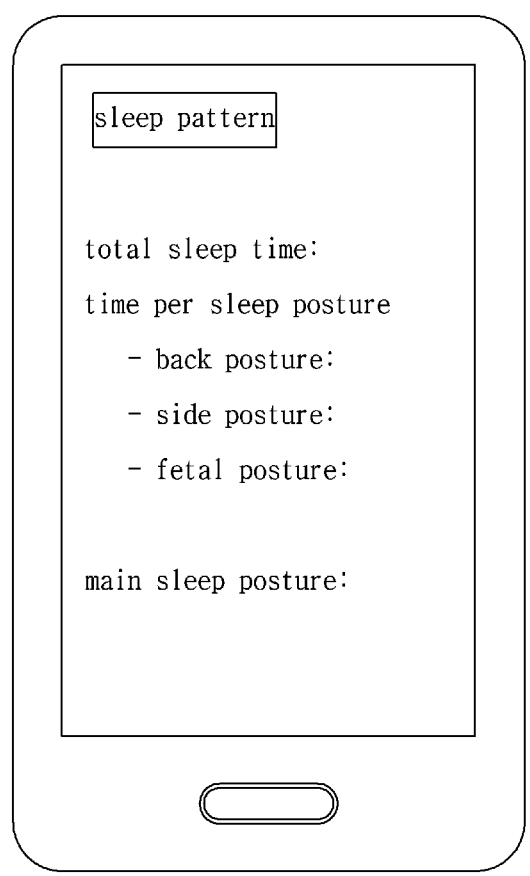

[FIG. 15]
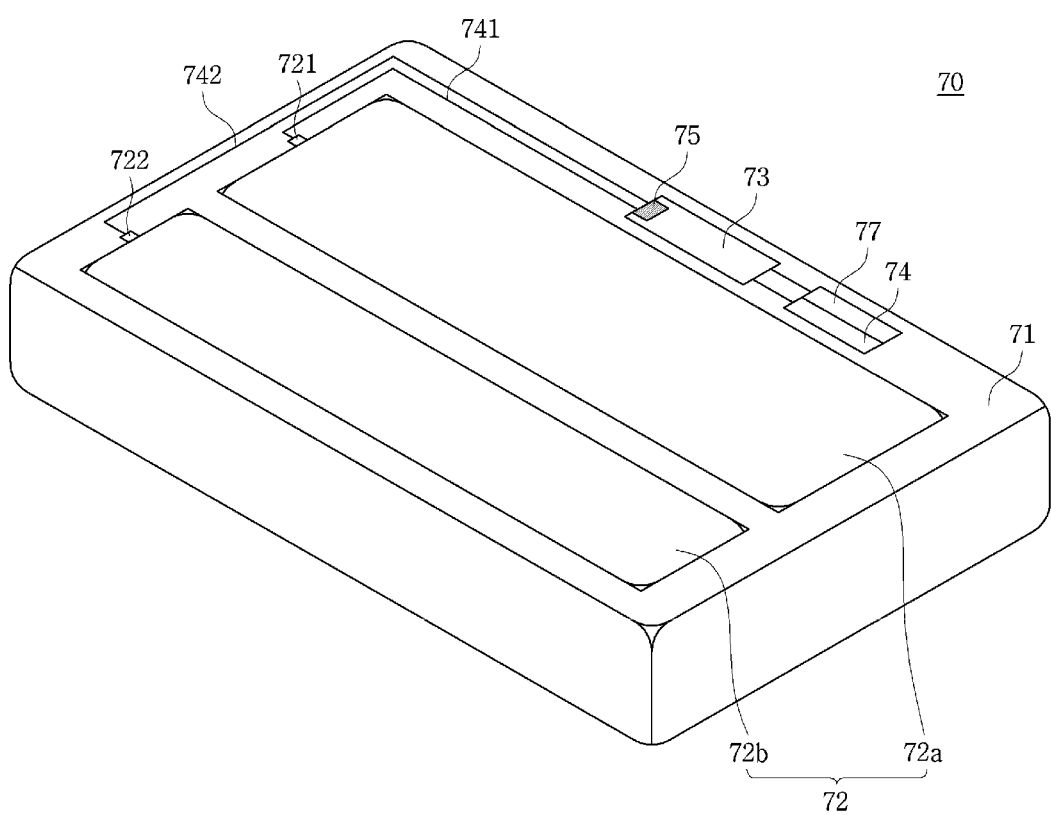

[FIG. 16]
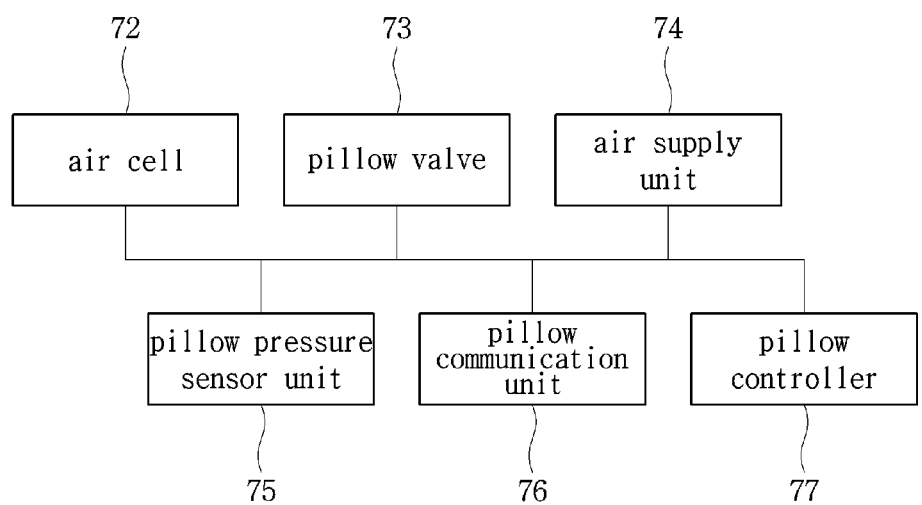

[FIG. 17]
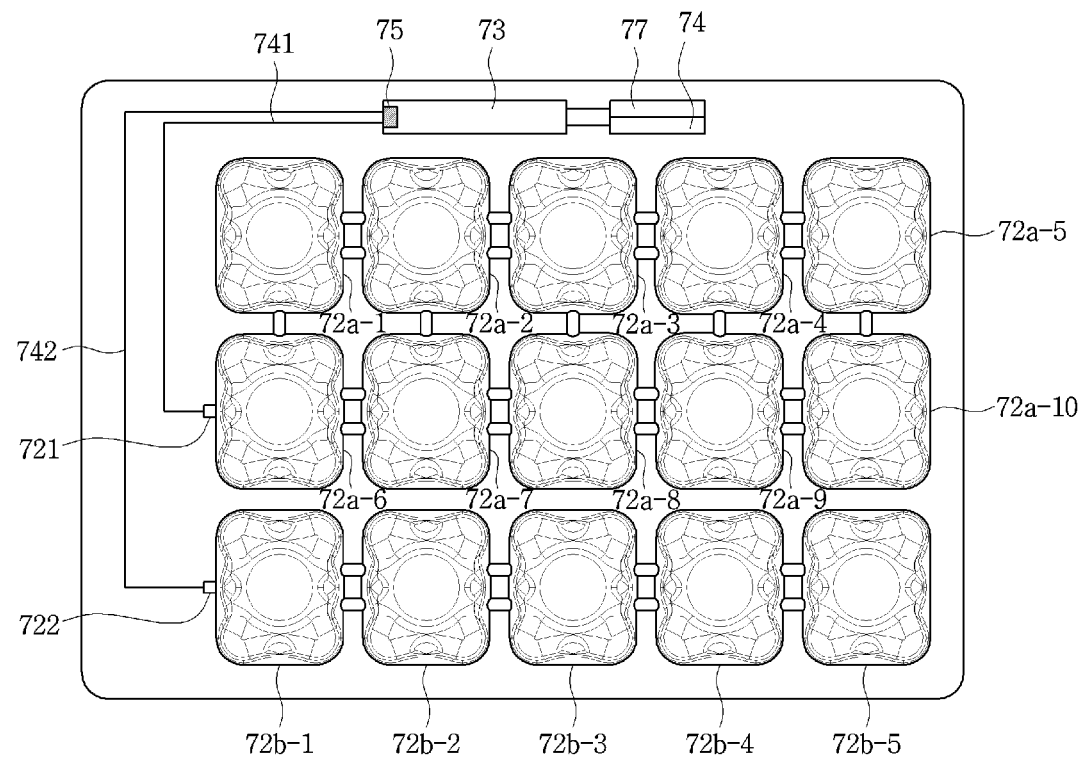

[FIG. 18]
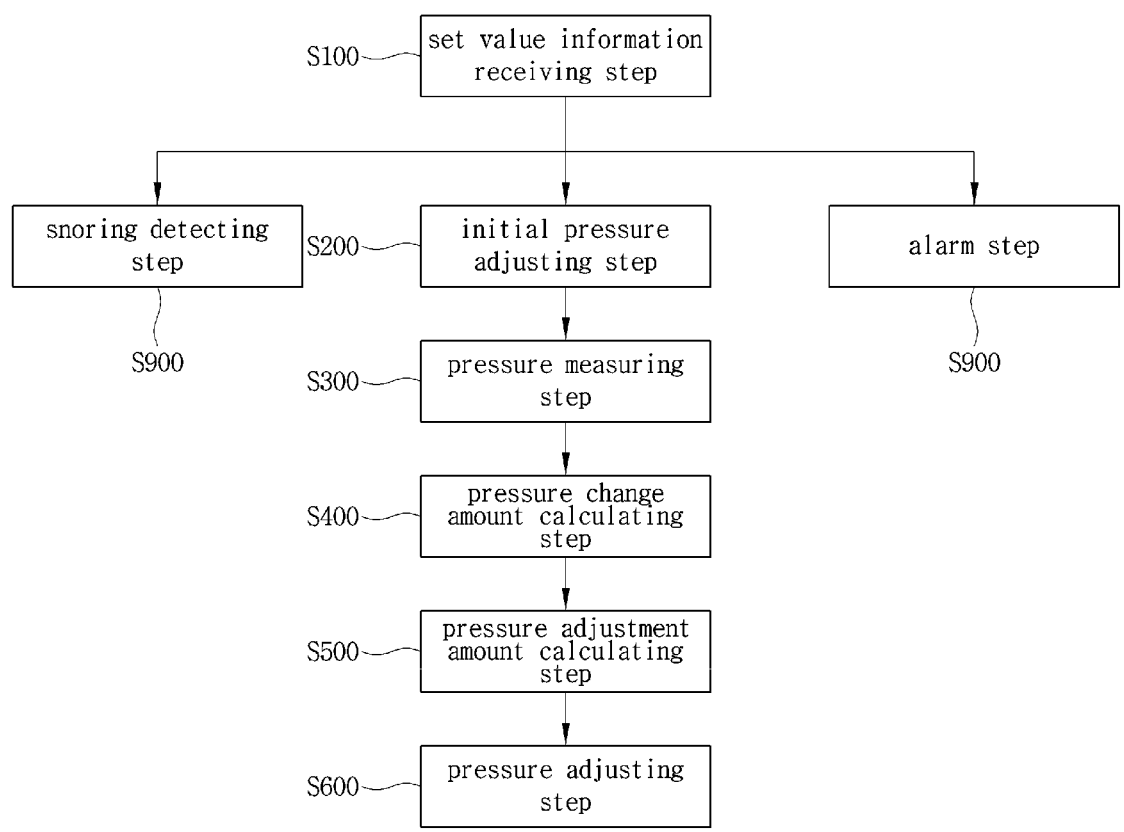

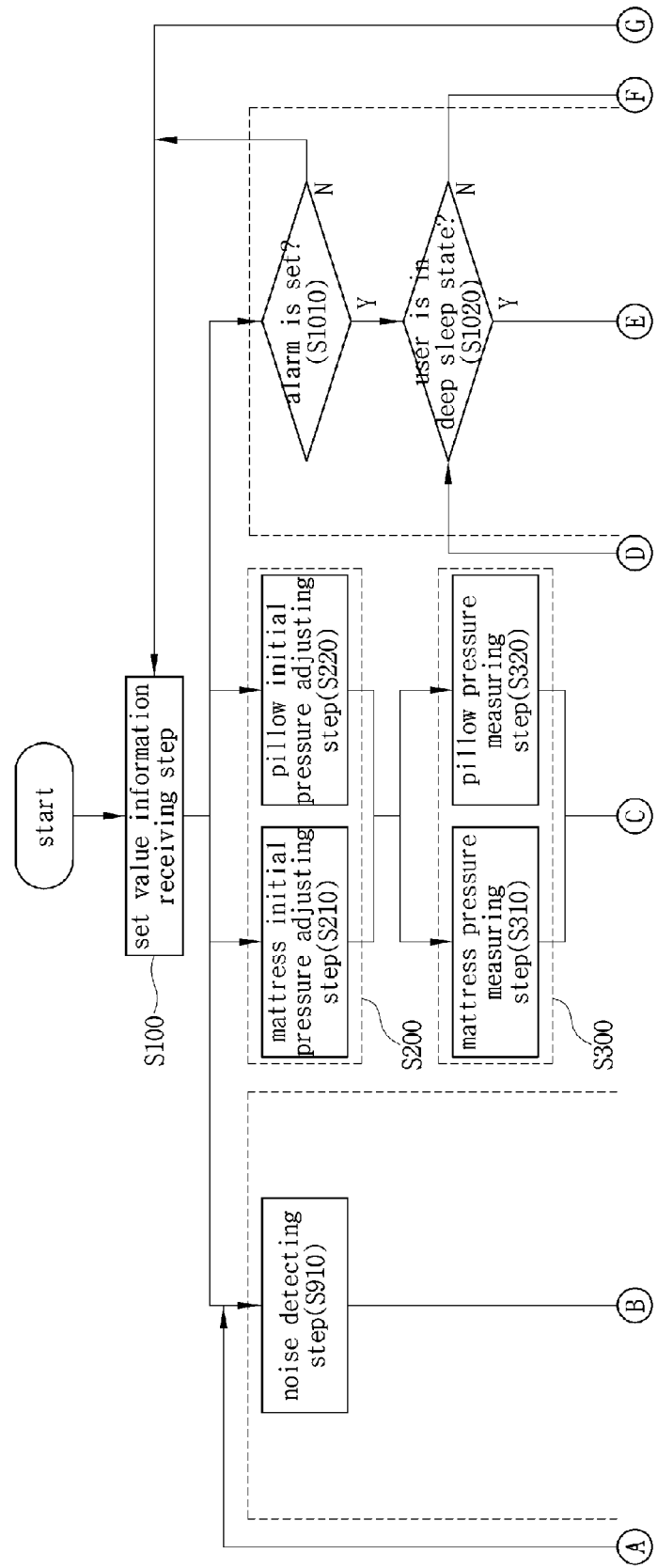
[FIG. 19]

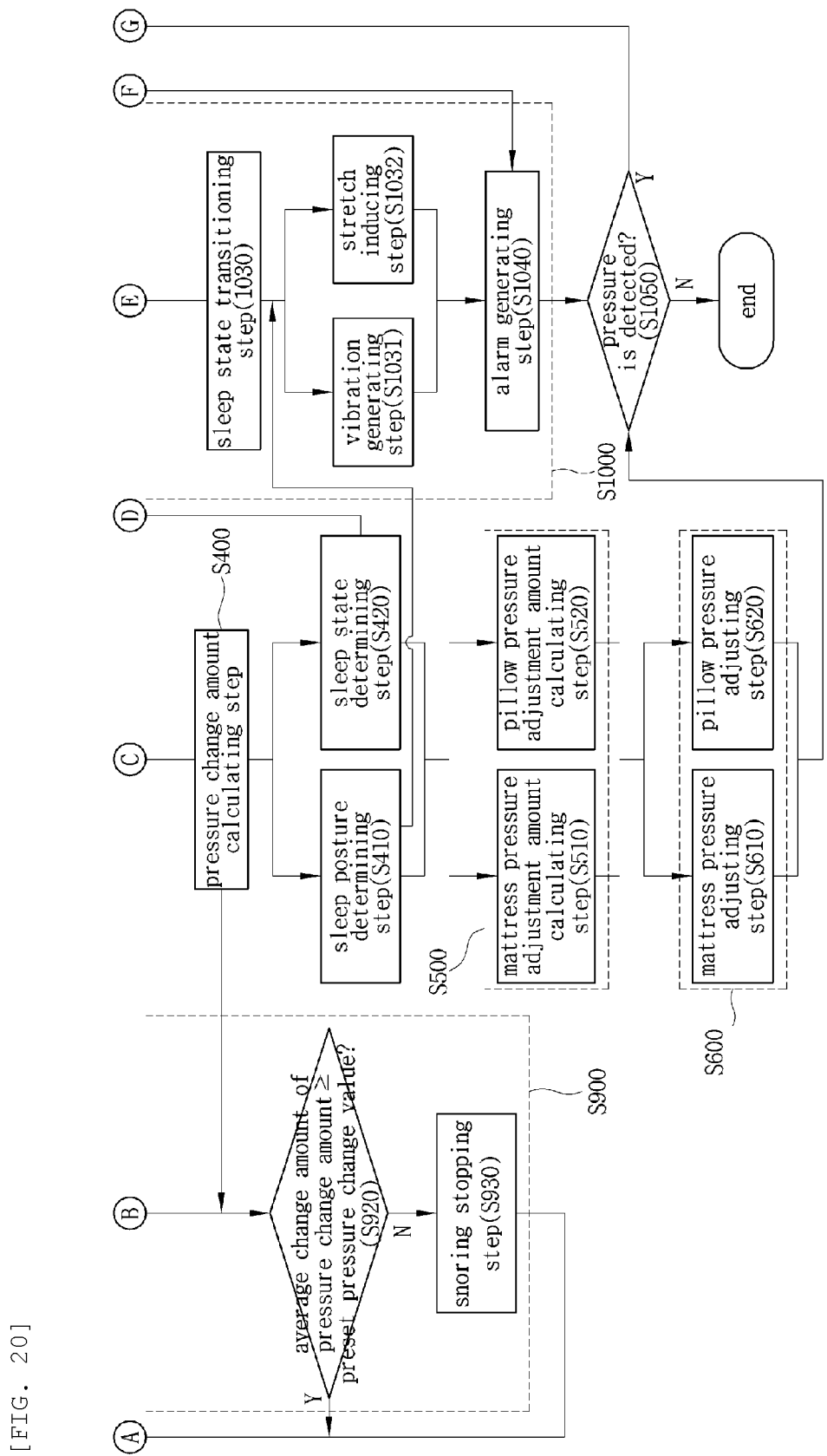
[FIG. 20]

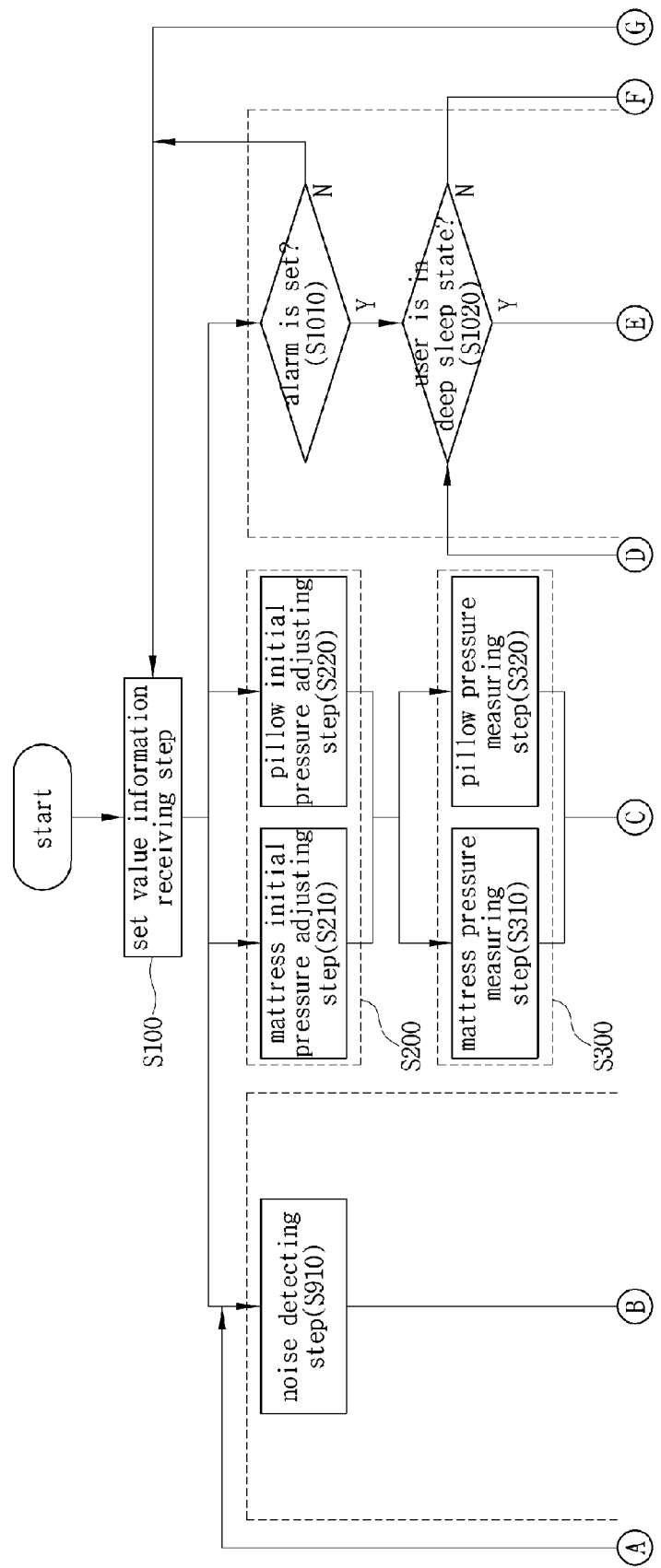
[FIG. 21]

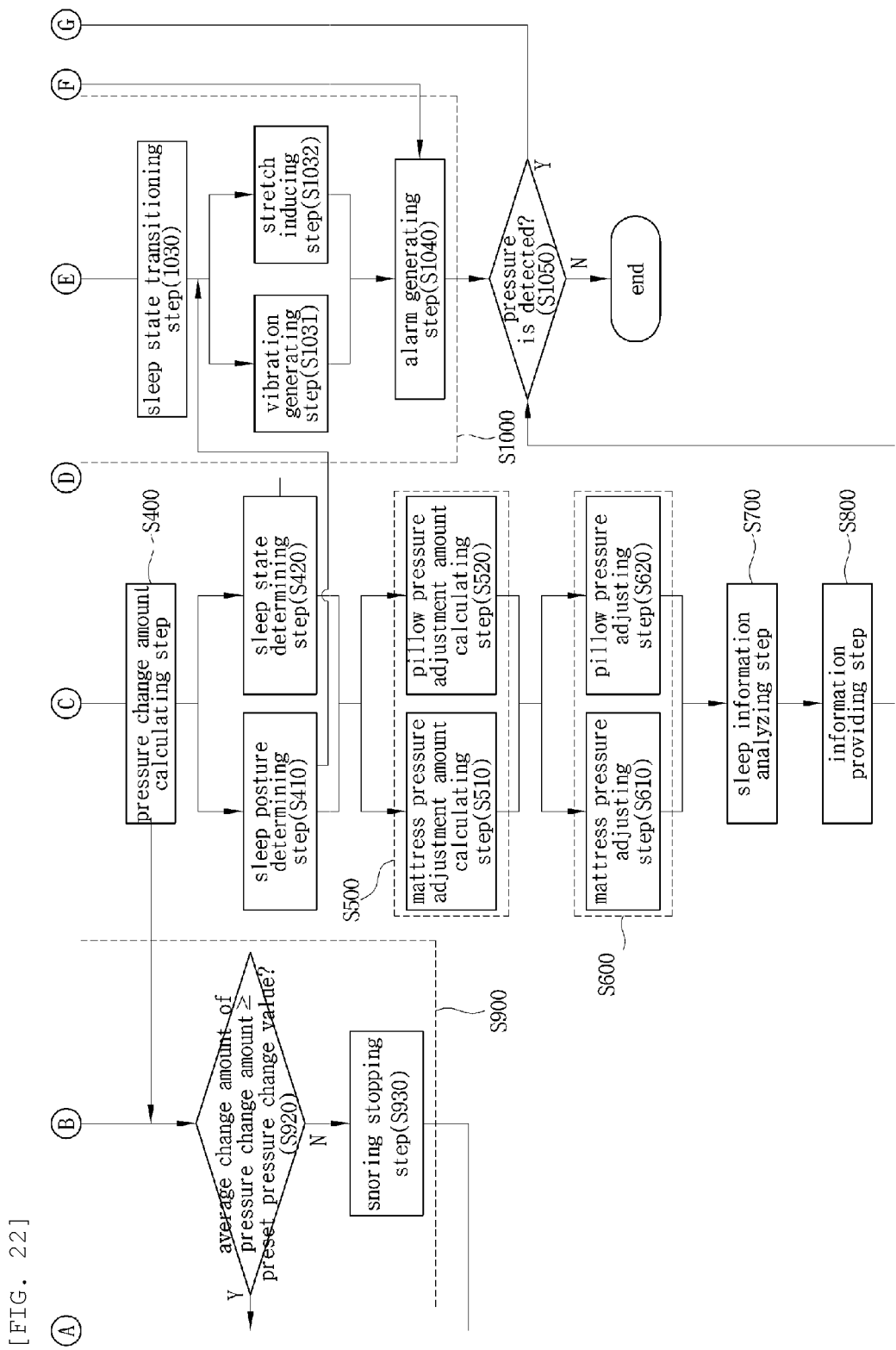
[FIG. 22]

METHOD FOR OPERATING SMART MATTRESS SYSTEM ENABLING ALARM CONTROL

TECHNICAL FIELD

The present invention relates to a method of operating a smart mattress system enabling alarm control, wherein a user is allowed to transition to a light sleep state before an alarm time set by the user.

BACKGROUND ART

In general, a mattress for a bed is a spring type mattress having a coil spring therein. However, the spring type mattress is problematic in that impacts applied to a local area of the mattress are transmitted to a surrounding area thus causing vibration. The spring type mattress is also problematic in that elasticity of the coil spring is set at the time of manufacturing so that a user may not arbitrarily adjust a degree of cushioning, and elasticity of the coil spring may be deteriorated after long-term use of the mattress.

In an effort to overcome the drawbacks of such a spring type mattress, an air mattress filled with air is used.

An air mattress is generally configured to have air injected thereinto to provide proper cushioning due to air pressure formed therein. The air mattress is comprised of a cushion portion having multiple air pockets, a bottom plate bonded to a lower surface of the cushion portion, and a frame assembly supporting a side surface of the cushion portion.

However, the air mattress in the related art is problematic in that changing of air pressure set at the time of manufacturing may be impossible. Thus, adjusting of pressure of the air mattress and pressure of an air pillow depending on a sleep posture of a user may be impossible.

Furthermore, it may be difficult for a user to adjust pressure of the air mattress as desired.

Furthermore, measuring and analyzing a sleep pattern and sleep quality of a user may be impossible.

Documents of Related Art

Korean Patent Application Publication No. 10-2003-0061267 (Jul. 18, 2003)

DISCLOSURE

Technical Problem

Accordingly, the present invention has been made keeping in mind the above problems occurring in the related art, and an objective of the present invention is to provide a method of operating a smart mattress system enabling alarm control, wherein a sleep posture of a user is determined such that pressure adjustment of an air mattress and pressure adjustment of the air pillow are possible depending on the sleep posture of the user.

Another objective of the present invention is to provide a method of operating a smart mattress system enabling alarm control, wherein an air mattress is divided into multiple sections according to a body part of a user and pressure of each section is measured, whereby a sleep posture of the user is measured.

A further objective of the present invention is to provide a method of operating a smart mattress system enabling alarm control, wherein an upper portion of an air pocket is protected such that the air pocket is prevented from being depressed due to the weight of a user.

A yet further objective of the present invention is to provide a method of operating a smart mattress system enabling alarm control, wherein an air mattress and the air pillow interlock with a user terminal such that a user easily controls the air mattress and the air pillow.

A still further objective of the present invention is to provide a method of operating a smart mattress system enabling alarm control, wherein analyzing of a sleep pattern and sleep quality of a user is possible.

Technical Solution

In order to accomplish the above objectives, according to one aspect of the present invention, there is provided a method of operating a smart mattress system enabling alarm control, the system including: an air mattress 10 configured to self-adjust its own pressure and to measure the pressure in real time; a user terminal 30 receiving a set value or user information from a user and transmitting the set value or the user information to the air mattress 10; a server 50 receiving measurement data from the air mattress 10 to analyze a sleep pattern and sleep quality of a user and transmitting the analyzed sleep pattern and sleep quality to the user terminal 30; and an air pillow 70 connected with the air mattress 10, the user terminal 30, and the server 50 and configured to self-adjust its own pressure, the method including: a set value information receiving step S100 of receiving, by the air mattress 10 and the air pillow 70, the set value including an initial pressure value, an alarm time, etc. or the user information including a body condition of the user from the user terminal 30; an initial pressure adjusting step S200 of individually adjusting pressure of an air pocket 110 of the air mattress 10 and pressure of an air cell 72 of the air pillow 70 based on the set value or the user information; a pressure measuring step S300 of respectively measuring, by a pressure sensor unit 14 and a pillow pressure sensor unit 75, in real time the pressure of the air pocket 110 and the pressure of the air cell 72 that change depending on a movement of the user; a pressure change amount calculating step S400 of calculating, by a pressure change amount calculating unit 19, a pressure change amount of the air pocket 110 based on a pressure measurement value measured in real time; a pressure adjustment amount calculating step S500 of individually calculating, by a pressure adjustment amount calculating unit 20, a pressure adjustment amount of the air pocket 110 and a pressure adjustment amount of the air cell 72 based on the calculated pressure change amount; a pressure adjusting step S600 of individually adjusting the pressure of the air pocket 110 and the pressure of the air cell 72 based on the pressure adjustment amounts calculated by the pressure adjustment amount calculating unit 20; and an alarm step S1000 of waking the user from sleeping, wherein the user is allowed to transition from a deep sleep (NREM sleep) state to a light sleep (REM sleep) state before a set alarm time.

Furthermore, the air mattress 10 may include: an air pocket unit 11 including multiple air pockets 110 each having a hollow portion formed therein and configured to inflate due to air inflow or to deflate due to air outflow; a body portion 12 into which the air pocket unit 11 is inserted; a mattress controller 13 mounted at the body portion 12 and controlling pressure of the air pocket unit 11; the pressure sensor unit 14 measuring the pressure of the air pocket unit 11 in real time; an air pump 15 supplying air into the air pockets 110; and a mattress communication unit 16 communicating with the user terminal 30, the server 50, and the air pillow 70.

Furthermore, the air mattress 10 may include: a sleep time measuring unit 18 measuring the sleep time based on a time that the user uses the air mattress 10; the pressure change amount calculating unit 19 calculating the pressure change amount of the air pocket unit 11 based on the pressure measurement value measured in real time by the pressure sensor unit 14 during the sleep time of the user; and the pressure adjustment amount calculating unit 20 calculating the pressure adjustment amount based on the calculated pressure change amount such that the pressure of the air pocket unit 11 is within an optimum air pocket pressure range ranging from a preset lower limit value L to a preset upper limit value H that are determined based on the set value and the user information.

Furthermore, the air pillow 70 may include: a cover 71 forming an appearance of the air pillow 70; an air cell 72 disposed inside the cover 71 and having a hollow portion formed therein, the air cell being configured to inflate air inflow or to deflate due to air outflow; a pillow valve 73 adjusting air supply to the air cell 72 or air discharge from the air cell 72; an air supply unit 74 supplying air to the air cell 72; the pillow pressure sensor unit 75 measuring the pressure of the air cell 72; a pillow communication unit 76 communicating with the air mattress 10, the user terminal 30, and the server 50; and a pillow controller 77 disposed inside the cover 71 and adjusting the pressure of the air cell 72.

Furthermore, the initial pressure adjusting step S200 may include: a mattress initial pressure adjusting step S210 of adjusting an initial pressure of the air pockets 110 based on the set value or the user information received in the set value information receiving step S100; and a pillow initial pressure adjusting step S220 of adjusting an initial pressure of the air cell 72 based on the set value or the user information received in the set value information receiving step S100.

Furthermore, the pressure measuring step S300 may include: a mattress pressure measuring step S310 of measuring the pressure of the air pockets 110 that changes in real time; and a pillow pressure measuring step S320 of measuring the pressure of the air cell 72 that changes in real time.

Furthermore, the method may further include: after the pressure change amount calculating step S400, a sleep posture determining step S410 of determining a sleep posture of the user based on the pressure change amount calculated in the pressure change amount calculating step S400; and a sleep state determining step S420 of determining whether a sleep state of the user is the deep sleep (NREM sleep) state or the light sleep (REM sleep) state based on an average change amount of the pressure change amount calculated in the pressure change amount calculating step S400.

Furthermore, the air mattress 10 may be configured such that the air pockets 110 arranged in multiple rows and multiple columns are divided into multiple sections, and the pressure sensor unit 14 may measure the pressure of the air pockets 110 for each section of the multiple sections.

Furthermore, the alarm step S1000 may include: an alarm setting checking step S1010 of checking whether an alarm is set by the user in the set value information receiving step S100; a sleep state checking step S1020 of when it is checked that the alarm is set in the alarm setting checking step S1010, checking whether the sleep state of the user is the deep sleep (NREM sleep) state or the light sleep (REM sleep) state from the sleep state determining step S420; a sleep state transitioning step S1030 of when the sleep state of the user checked in the sleep state checking step S1020 is the deep sleep (NREM sleep) state, adjusting the pressure of the air pockets 110 or the air cell 72 to allow the user to transition from the deep sleep (NREM sleep) state to the light sleep (REM sleep) state before a preset alarm time T5 from the alarm time; and an alarm generating step S1040 of generating an alarm at the alarm time received in the set value information receiving step S100 after the user has transitioned to the light sleep (REM sleep) state.

Furthermore, the sleep state transitioning step S1030 may include a vibration generating step S1031 of repeating air inflow and air discharge of the air pockets 110 or the air cell 72 to apply vibration to the user, thereby allowing the user to transition from the deep sleep (NREM sleep) state to the light sleep (REM sleep) state, wherein the multiple air pockets 110 simultaneously repeatedly perform air inflow and air discharge or multiple air cells 72 simultaneously repeatedly perform air inflow and air discharge to generate the vibration.

Furthermore, the sleep state transitioning step S1030 may further include a stretch inducing step S1032 of allowing air inflow and air discharge of the air pockets 110 to be performed differently for each section or allowing air inflow and air discharge of the multiple air cells 72 to be performed differently for each cell, thereby inducing a user to stretch his or her body.

Furthermore, the method may further include: a sleep information analyzing step S700 of receiving, by the server 50, the measurement data including the pressure measurement value, the pressure change amount, the sleep time, and the pressure adjustment amount for each section from the air mattress 10 to analyze the sleep pattern and the sleep quality of the user; and an information providing step S800 of receiving, by the user terminal 30, user's sleep information analyzed by the server 50 to provide the sleep information to the user.

Furthermore, the server 50 may include: a server controller 51 controlling the server 50; a server communication unit 52 communicating with the air mattress 10, the user terminal 30, and the air pillow 70; a server memory unit 53 storing data received from the air mattress 10, the user terminal 30, and the air pillow 70 and data transmitted to the air mattress 10, the user terminal 30, and the air pillow 70; a sleep pattern analyzing unit 54 receiving the measurement data including the pressure measurement value, the pressure change amount, the sleep time, and the pressure adjustment amount for each section from the air mattress 10 and analyzing the sleep time and the sleep posture based on the measurement data; and a sleep quality analyzing unit 55 receiving the measurement data including the pressure measurement value, the pressure change amount, the sleep time, and the pressure adjustment amount for each section from the air mattress 10, classifying the sleep state of the user into the deep sleep (NREM sleep) state, the light sleep (REM sleep) state, and a wake state, determining the sleep state based on the measurement data, and scoring the sleep quality.

Furthermore, the sleep information analyzing step S700 may include a sleep pattern analyzing step S710 of analyzing, by the server 50, a sleep posture and the sleep time based on the measurement data received from the air mattress 10.

Furthermore, the sleep information analyzing step S700 may include: a sleep quality analyzing step S730 of dividing, by the server 50, the sleep state of the user into the deep sleep state, the light sleep state, and the wake state based on the measurement data received from the air mattress 10, determining the sleep state based on the measurement data, and analyzing the sleep quality.

Advantageous Effects

As described above, according to the embodiment of the present invention, a sleep posture of a user is determined such that pressure adjustment of the air mattress and pressure adjustment of the air pillow are possible depending on the sleep posture of the user.

Furthermore, the air mattress is divided into multiple sections according to a body part of a user and pressure of each section is measured, whereby a sleep posture of the user can be measured.

Furthermore, an upper portion of the air pocket is protected such that the air pocket can be prevented from being depressed due to the weight of a user.

Furthermore, the air mattress and the air pillow interlock with the user terminal such that a user can easily control the air mattress and the air pillow.

Furthermore, analyzing of a sleep pattern and sleep quality of a user is possible.

DESCRIPTION OF DRAWINGS

FIG. 1 is a perspective view showing an air pocket module according to an embodiment of the present invention.

FIG. 2 is a perspective view showing an air pocket according to FIG. 1.

FIG. 3 is a plan view showing the air pocket according to FIG. 2.

FIG. 4 is a plan view showing the air pocket module according to FIG. 1.

FIG. 5 is a plan view showing an air pocket unit according to the embodiment of the present invention.

FIG. 6 is a bottom view showing the air pocket unit according to FIG. 5.

FIG. 7 is a view schematically showing a smart mattress system enabling alarm control according to the embodiment of the present invention.

FIG. 8 is a view showing an air mattress according to the embodiment of the present invention.

FIG. 9 is a view schematically showing the air mattress according to the embodiment of the present invention.

FIG. 10 is a view showing another embodiment of a pressure sensor unit of the air mattress according to FIG. 9.

FIG. 11 is a block diagram schematically showing a configuration of the air mattress according to the embodiment of the present invention.

FIG. 12 is a block diagram schematically showing a configuration of a server according to the embodiment of the present invention.

FIG. 13*a* is a graph showing a pressure change rate as a function of time in order to score sleep quality according to the embodiment of the present invention.

FIG. 13*b* is a view showing a formula for scoring the sleep quality according to FIG. 13*a*.

FIG. 14*a* is a view showing a setting screen of a user terminal according to the embodiment of the present invention.

FIG. 14*b* is a view showing a sleep quality score screen of the user terminal according to the embodiment of the present invention.

FIG. 14*c* is a view showing a sleep pattern analysis screen of the user terminal according to the embodiment of the present invention.

FIG. 15 is a perspective view showing the air pillow according to the embodiment of the present invention.

FIG. 16 is a block diagram showing a configuration of the air pillow according to the embodiment of the present invention.

FIG. 17 is a plan view showing an air pillow according to another embodiment of the present invention.

FIGS. 18 to 22 are flowcharts showing a method of operating the smart mattress system enabling alarm control according to the embodiment of the present invention.

BEST MODE

Hereinafter, exemplary embodiments of the present invention will be described in detail with reference to the accompanying drawings. It should be noted that the embodiments of the present invention are disclosed only for illustrative purposes and should not be construed as limiting the present invention.

In the following description of the present invention, detailed descriptions of known functions and components incorporated herein will be omitted when it may make the subject matter of the present invention unclear. Furthermore, technical terms, as will be mentioned hereinafter, are terms defined in consideration of their function in the present invention, which may be varied according to the intention of a user, practice, or the like, so that the terms should be defined based on the contents of this specification.

The technical sprit of the present invention is defined by the accompanying claims, and the following embodiments are presented for those skilled in the art to be able to more clearly understand the spirit of the present invention.

FIG. 1 is a perspective view showing an air pocket module according to an embodiment of the present invention, FIG. 2 is a perspective view showing an air pocket according to FIG. 1, and FIG. 3 is a plan view showing the air pocket according to FIG. 2.

Referring to FIGS. 1 to 3, an air pocket module 100 is inserted into an air mattress 10 on which a user sits or lies down. Specifically, the air pocket module 100 is used for an air mattress 10 for a bed.

The air pocket module 100 includes multiple air pockets 110 and a bottom plate 130.

Each of the air pockets 110 has a hollow portion formed therein and is configured to inflate due to air inflow or deflate due to air outflow. The air pocket 110 includes multiple surfaces.

Herein, referring to FIGS. 2 and 3, the air pocket 110 includes a top surface portion 1110, a side surface portion 1120, a first connection portion 1130, a contact portion 1140, a first inflation portion 1151, a second inflation portion 1152, a first reinforcing portion 1171, a second reinforcing portion 1172, and a second connection portion 1180.

The top surface portion 1110 forms a top surface of the air pocket 110. The top surface portion 1110 is a portion that supports a user when a user lies on the air mattress 10, and may be a portion that directly receives a load of a user. The top surface portion 1110 is depressed due to the load of a user.

The side surface portion 1120 is connected with the top surface portion 1110 to form a side surface of the air pocket 110.

In the present embodiment, the side surface portion 1120 is comprised of a total of four surfaces, and the top surface portion 1110 has a rectangular shape without being limited thereto. However, the side surface portion 1120 may include five side surfaces, and the top surface portion 1110 may have a pentagonal shape or various other shapes.

The side surface portion 1120 includes a first side surface 1121 and a second side surface 1122. Specifically, the side surface portion 1120 is comprised of four surfaces, and two facing surfaces of the four surfaces are referred to as first side surfaces 1121, and another two facing surfaces are referred to as second side surfaces 1122.

The first connection portion 1130 is formed at an edge portion where the top surface portion 1110 and the side surface portion 1120 are connected to each other to connect the top surface portion 1110 and the side surface portion 1120 to each other. In other words, the first connection portion 1130 is formed at the edge portion where the top surface portion 1110 and the side surface portion 1120 are connected to each other. The first connection portion 1130 is inclined from the top surface portion 1110 toward the side surface portion 1120.

The inclined first connection portion 1130 disperses the load of a user applied to the top surface portion 1110 and prevents deformation or depression of the top surface portion 1110 pressed by the load of a user. Specifically, the top surface portion 1110, which receives the load of a user, is pressed toward the bottom plate 130, that is, inwardly of the air pocket 110 due to the load of a user. Herein, in a case where the top surface portion 1110 and the side surface portion 1120 are directly vertically connected to each other, when the top surface portion 1110 is pressed inwardly of the air pocket 110 due to the load, a height difference occurs at the edge portion where the top surface portion 1110 and the side surface portion 1120 are connected to each other. When such a height difference occurs repeatedly, the edge portion may be easily depressed and the air pocket 110 may be broken. To prevent this, the first connection portion 1130 is formed to have a predetermined inclination. Even when the top surface portion 1110 receives the load, the height difference is reduced due to the inclination of the first connection portion 1130. Thus, the top surface portion 1110 and the side surface portion 1120 can be prevented from being depressed or broken due to a load.

The contact portion 1140 is a portion that protrudes upwards from a center of the top surface portion 1110 to support a user. In other words, the contact portion 1140 protrudes upwards from the top surface portion 1110 by a predetermined height difference therebetween. Thus, pressure applied to the top surface portion 1110 due to the load of a user is dispersed whereby the top surface portion 1110 can be protected from depression or deformation. Herein, the predetermined height difference may indicate a degree that a user does not feel discomfort when lying on the air mattress 10.

Specifically, in order to prevent the top surface portion 1110 directly receiving the load from being depressed, the contact portion 1140 protrudes from the center of the top surface portion 1110. Thus, when a user sits down or lies on the air mattress 10, the load of a user is applied firstly to the contact portion 1140. The load of a user is applied firstly to the contact portion 1140 and is then applied to the top surface portion 1110. In addition, since the contact portion 1140 protrudes, the top surface portion 1110 is directly depressed by the load of a user. Thus, when a user sits down or lies on the air mattress 10, the contact portion 1140 can protect the top surface portion 1110 against the load of a user that is applied to the air pocket 110.

The first inflation portion 1151 is included in the first side surface 1121. The first inflation portion 1151 is concavely formed toward the hollow portion such that when the air pockets 110 inflate, the side surface portions 1120 of each of the multiple air pockets 110 and an adjacent air pocket are prevented from coming into contact with each other.

The second inflation portion 1152 is included in the second side surface 1122. The second inflation portion 1152 is concavely formed toward the hollow portion such that when the air pockets 110 inflate, the side surface portions 1120 of each of the multiple air pockets 110 and an adjacent air pocket are prevented from coming into contact with each other. Furthermore, multiple second inflation portions 1152 are formed on each of the second side surfaces 1122.

Specifically, when air is supplied into the air pockets 110, the air pockets 110 inflate. When adjacent air pockets 110 inflate and come into contact with each other, a desired pressure of each air pocket 110 is inhibited from being formed. To prevent this, the first inflation portion 1151 and the second inflation portion 1152 are formed on the side surface portion 1120 to be concavely formed toward the hollow portion of the air pocket 110 at a predetermined depth.

The support portion 1160 is included in the second side surface 1122. The support portion 1160 protrudes outwardly of the air pocket 110 at a position between the multiple second inflation portions 1152 formed on each of the second side surfaces 1122. In other words, the support portion 1160 is formed between the two second inflation portions 1152. The support portion 1160 has an upper end connected with the contact portion 1140 to improve supportability of the contact portion 1140.

The first reinforcing portion 1171 is included in the first side surface 1121. The first reinforcing portion 1171 is inclined inwardly from the first connection portion 1130 toward a lower end of the first side surface 1121. In addition, the first reinforcing portion 1171 is configured such that a width thereof gradually decreases from the first connection portion 1130 to a lower portion of the first side surface 1121.

The second reinforcing portion 1172 is included in the second side surface 1122. The second reinforcing portion 1172 is inclined inwardly from the first connection portion 1130 toward a lower end of the support portion 1160. The second reinforcing portion 1172 is configured such that a width thereof gradually decreases from the first connection portion 1130 to a lower portion of the support portion 1160.

The first reinforcing portion 1171 and the second reinforcing portion 1172 prevent the air pocket 110 from collapsing or being abnormally depressed as stress is concentrated on the edge portion (i.e., the first connection portion 1130) where the top surface portion 1110 and the side surface portion 1120 are connected to each other due to the load of a user applied thereto. In other words, the first reinforcing portion 1171 and the second reinforcing portion 1172 prevent deformation of the top surface portion 1110 from the load applied to the top surface portion 1110, thereby improving strength of the air pocket 110.

The first reinforcing portion 1171 and the second reinforcing portion 1172 are formed in a groove shape such that widths thereof gradually decrease from the first connection portion 1130 to a lower portion of the side surface portion 1120. A reinforcing portion 1170 is formed in a protrusion shape, but it is preferable that the reinforcing portion 1170 is formed in a groove shape because the protrusion shape may cause user discomfort.

The second connection portion 1180 is connected to a lower portion of the air pocket 110 and the bottom plate 130.

The second connection portion 1180 is formed to be inclined outwardly from a peripheral end of the air pocket 110 toward the bottom plate 130.

The bottom plate 130 is coupled to lower sides of the multiple air pockets 110 to block hollow portions of the air pockets 110. The bottom plate 130 may have a plate shape. The bottom plate 130 is provided with a nozzle 131 (see FIG. 6) through which air is supplied and discharged to and from the air pockets 110. A detailed description of the nozzle 131 will be given later with reference to FIG. 6.

FIG. 4 is a plan view showing an air pocket module according to FIG. 1.

Referring to FIG. 4, the air pocket module 100 includes the multiple air pockets 110. Specifically, the multiple air pockets 110 are arranged in each of horizontal and vertical directions to form multiple rows and multiple columns, thereby forming one air pocket module 100.

In the present embodiment, the air pocket module 100 including the air pockets 110 arranged in four rows×five columns will be described as an example.

The air pocket module 100 includes a flow passage 140 communicating with the multiple air pockets 110. Specifically, the flow passage 140 includes a first flow passage 141 and a second flow passage 142.

The first flow passage 141 allows adjacent air pockets 110 in each row to communicate with each other. In other words, the first flow passage 141 allows adjacent air pockets 110 arranged in the horizontal direction to communicate with each other. At least one first flow passage 141 is provided between adjacent air pockets 110. It is preferable that two first flow passages 141 are provided between adjacent air pockets 110.

The second flow passage 142 allows adjacent air pockets 110 in each column to communicate with each other. In other words, the second flow passage 142 allows adjacent air pockets 110 arranged in the vertical direction to communicate with each other.

The first flow passage 141 is provided in each of a first row, a second row, a third row, and a fourth row. The second flow passage 142 is provided between the first row and the second row to allow the air pockets 110 in the first row and the second row to communicate with each other. In other words, the first row, the second row, the third row, and the fourth row of the air pocket module 100 are configured such that the air pockets 110 arranged in each row are allowed to communicate with each other by the first flow passage 141. Furthermore, the second flow passage 142 is provided between the first row and the second row to allow the first row and the second row to communicate with each other.

FIG. 5 is a plan view showing an air pocket unit according to the embodiment of the present invention.

Referring to FIG. 5, the air mattress 10 includes an air pocket unit 11.

The air pocket unit 11 includes at least one air pocket module 100. Specifically, the air pocket unit 11 includes a pair of air pocket modules 100.

The pair of air pocket modules 100 includes a first air pocket module 100*a* and a second air pocket module 100*b*. The first air pocket module 100*a* and the second air pocket module 100*b* are disposed such that row arrangements of the air pockets 110 of the first and second air pocket modules are symmetrical with each other.

Specifically, the first air pocket module 100*a* is disposed. Then, the second air pocket module 100*b* is disposed in contact with the first air pocket module 100*a* such that the row arrangement thereof is symmetrical with the row arrangement of the first air pocket module 100*a*.

Referring to the air pocket unit 11 in which the first air pocket module 100*a* and the second air pocket module 100*b* are in contact with each other, a first row and a second row of the first air pocket module 100*a* are allowed to communicate with each other by the second flow passage 142, while a third row and a fourth row of the second air pocket module 100*b* are allowed to communicate with each other by the second flow passage 142.

Hereinafter, with reference to FIG. 5, the air pocket unit 11 including the air pockets 110 arranged in eight rows×five columns will be described as an example.

The air pocket unit 11 is configured such that the multiple air pockets 110 in each of the first to eighth rows are allowed to communicate with each other by the first flow passage 141. In addition, the first row and the second row are allowed to communicate with each other by the second flow passage 142, and the seventh row and the eighth row are allowed to communicate with each other by the second flow passage 142.

The air pocket unit 11 composed of eight rows×five columns is divided into multiple sections. Herein, the air pocket unit is divided into the multiple sections depending on a position where the body part of a user is located.

As an example, the air pocket unit 11 is divided into a first section 11-1, a second section 11-2, a third section 11-3, and a fourth section 11-4.

The first section 11-1 is where a user's shoulder is located and is formed by at least one row of the air pocket unit 11.

The second section 11-2 is where a user's waist is located and is formed by at least one row of the air pocket unit 11.

The third section 11-3 is where user's buttocks are located and is formed by at least one row of the air pocket unit 11.

The fourth section 11-4 is where user's thighs and knees are located and is formed by multiple rows of the air pocket unit 11.

In the present embodiment, as an example, the first section 11-1 is formed by two rows, the second section 11-2 is formed by one row, the third section 11-3 is formed by two rows, and the fourth section 11-4 is formed by three rows.

A fifth section (not shown) may be where user's head or user's feet are located. The section where the user's head is located may be provided as a general mat without having the air pockets 110 being arranged. In general, the section where the user's head is located may not be provided with the air pockets 110 because a user may use a pillow or a pressure change of the air pockets may not be required. Likewise, the section where the user's feet are located may also not have the air pockets 110 being arranged. However, the present invention is not limited thereto, and the air pockets 110 may be arranged in the section where the user's head or user's feet are located, and the pressure of the air pockets may be adjusted.

In addition, an interval between each row of the air pockets 110 arranged in the air pocket unit 11 may be 150 mm. This is an interval such that the air pockets 110 may not interfere with each other when adjacent ones of the air pockets 110 inflate. Furthermore, an interval between each column may be 125 mm without being limited thereto.

FIG. 6 is a view showing the bottom plate of the air pocket unit according to FIG. 5.

Referring to FIG. 6, the bottom plate 130 is provided with the nozzle 131, a supply line 132, a valve 133, and a section connection line 134.

The nozzle 131 may be an inlet for allowing air to be supplied to and discharged from the air pockets 110. At least one nozzle 131 is provided in each of the first section 11-1, the second section 11-2, the third section 11-3, and the fourth section 11-4. Since the nozzle 131 is provided in each section, the pressure of the air pockets 110 is adjusted for each section of the air pocket unit 11.

However, in the present embodiment, one nozzle 131 communicating with the supply line 132 is provided for each section, but the present invention is not limited thereto. For example, multiple nozzles 131 may be provided in a section where pressure change of the air pockets 110 is large. In the third section 11-3 where the user's buttocks are located and the fourth section 11-4 where the user's thighs and knees are located, there is a large pressure change due to a large body load. Accordingly, the multiple nozzles 131 may be provided in the third section 11-3 and the fourth section 11-4. For example, two nozzles 131 are arranged in the first section 11-1, one nozzle 131 is arranged in the second section 11-2, three nozzles 131 are arranged in the third section 11-3, and two nozzles 131 are arranged in the fourth section 11-4. Furthermore, the nozzle 131 may be arranged at each of opposite sides of the bottom plate 130.

In addition, the nozzle 131 communicates with the section connection line 134 as well as the supply line 132. For example, multiple nozzles 131 are provided in the third section 11-3 to allow the fourth row and the fifth row, which do not communicate with each other, to communicate with each other. Likewise, multiple nozzles 131 are provided in each of the sixth row and the seventh row to allow the sixth row and the seventh row, which do not communicate with each other, to communicate with each other.

The supply line 132 connects the nozzle 131 and the valve 133 with each other. Multiple supply lines 132 communicate with multiple nozzles 131, respectively. Each of the supply lines 132 is configured such that air supply and air discharge to and from the air pockets 110 are switched by the valve 133.

The valve 133 adjusts air supply from an air pump (see FIG. 9) to the air pockets 110 and air discharge from the air pockets 110. The valve 133 may be a solenoid valve. However, the present invention is not limited thereto and may include various types of valves 133.

The section connection line 134 allows a row of the third section 11-3 and a row of the fourth section 11-4, which do not communicate with each other by the second flow passage 142, to communicate with each other.

Specifically, the section connection line 134 allows the fourth row and the fifth row of the third section 11-3, which do not communicate with each other, to communicate with each other. In other words, the section connection line 134 is connected to the nozzle 131 provided in each of the fourth row and the fifth row so as to allow the fourth row and the fifth row of the air pockets 110 to communicate with each other.

Likewise, the section connection line 134 allows the sixth row and the seventh row of the fourth section 11-4, which do not communicate with each other, to communicate with each other. In other words, the section connection line 134 is connected to the nozzle 131 provided in each of the sixth row and the seventh row so as to allow the rows of air pockets 110 in the fourth section 11-4 to communicate with each other.

FIG. 7 is a view schematically showing a smart mattress system enabling alarm control according to the embodiment of the present invention.

Referring to FIG. 7, a smart mattress system 1 enabling alarm control includes an air mattress 10, a user terminal 30, a server 50, and an air pillow 70.

The air mattress 10 includes the air pocket unit 11 described above and is capable of adjusting the pressure of the air pockets 110 of the air pocket unit 11. Specifically, the pressure of the air pockets 110 of the air mattress 10 is adjusted for each section of the multiple sections based on a set value or user information set and input by a user.

The user terminal 30 receives the set value including an initial pressure value, an alarm setting, etc. or the user information including user's body information such as a user's weight, height, etc. from a user. The user terminal 30 transmits the set value or the user information received from a user to the air mattress 10 or the air pillow 70. The user terminal 30 may be any one of a notebook computer, a computer, and a mobile phone.

The server 50 receives measurement data from the air mattress 10, analyzes a sleep pattern and sleep quality of a user, and transmits the analyzed sleep pattern and sleep quality to the user terminal 30.

The air pillow 70 is connected to the air mattress 10, the user terminal 30, and the server 50. The air pillow 70 is configured to self-adjust its own pressure. In particular, when a sleep posture of a user is ascertained based on a pressure measurement value measured by the air mattress 10, the pressure of the air pillow 70 is adjusted thereby.

The air mattress 10, the server 50, and the air pillow 70 will be described in detail later.

FIG. 8 is a view showing an air mattress according to the embodiment of the present invention, FIG. 9 is a view schematically showing the air mattress according to the embodiment of the present invention, and FIG. 10 is a view showing another embodiment of a pressure sensor unit of the air mattress according to FIG. 9.

Referring to FIGS. 8 to 10, an air mattress 10 includes an air pocket unit 11, a body portion 12, a mattress controller 13, a pressure sensor unit 14, and an air pump 15.

At least one air pocket unit 11 is inserted into the body portion 12. In the present embodiment, two air pocket units 11 inserted into the body portion 12 are described as an example. Specifically, a first air pocket unit 11L and a second air pocket unit 11R are respectively arranged at left and right sides of the body portion 12. The first air pocket unit 11L and the second air pocket unit 11R are individually controlled by the mattress controller 13.

The body portion 12 forms the overall shape of the air mattress 10, and the air pocket unit 11 is inserted thereinto. The body portion 12 is provided with an air pocket unit fixing portion 121 where the air pocket unit 11 is inserted. In addition, the body portion is provided with a controller fixing portion 122 where the mattress controller 13 is mounted.

The mattress controller 13 is mounted at the body portion 12. The mattress controller 13 controls the air mattress 10. Specifically, the mattress controller adjusts the pressure of the air pocket unit 11. The mattress controller 13 adjusts the pressure of the multiple air pockets 110 arranged in each of the first section 11-1, the second section 11-2, the third section 11-3, and the fourth section 11-4.

In addition, the mattress controller 13 individually controls the first air pocket unit 11L and the second air pocket unit 11R respectively arranged at the left and right sides of the body portion 12.

The pressure sensor unit 14 measures the pressure of the air pocket unit 11.

The pressure sensor unit 14 measures the pressure of the air pockets 110 and possibly measures the pressure of each section of the first section 11-1, the second section 11-2, the third section 11-3, and the fourth section 11-4.

Based on the pressure measured by the pressure sensor unit 14, the mattress controller 13 controls air supply and air discharge to and from the air pockets 110 in each of the first section 11-1, the second section 11-2, the third section 11-3, and the fourth section 11-4 to adjust the pressure of the air pockets 110.

Referring to FIG. 9, one pressure sensor unit 14 is provided. In this case, the pressure sensor unit 14 is connected with a main supply line 1321 to measure the pressure of each of the supply lines 132.

Referring to FIG. 10, the pressure sensor unit 14 is provided in the valve 133 and is connected to each of the supply lines 132. The pressure sensor unit 14 connected to the supply line 132 measures the pressure of the air pockets 110 in each section.

Based on the pressure measured by the pressure sensor unit 14, the mattress controller 13 adjusts the pressure of the air pockets 110.

The air pump 15 supplies air to the air pockets 110 through the supply lines 132.

FIG. 11 is a block diagram schematically showing a configuration of the air mattress according to the embodiment of the present invention.

Referring to FIG. 11, the air mattress 10 includes a mattress communication unit 16, a mattress memory unit 17, a sleep time measuring unit 18, a pressure change amount calculating unit 19, a pressure adjustment amount calculating unit 20, a custom pressure calculating unit 21, a microphone 22, and a snoring determination unit 23.

The mattress communication unit 16 communicates with the user terminal 30 and the server 50 to transmit and receive data. The mattress communication unit 16 receives the set value or the user information from the user terminal 30. Herein, the set value may be a set value for setting the condition and environment of the air mattress 10, the set value including pressure intensity desired by a user, a sleep time, etc, and the user information may be information related to a user's body, the user information including the height, weight, clothing size, health condition, etc. of a user.

The mattress communication unit 16 is connected with a server communication unit 52 (see FIG. 12) and transmits the measurement data to the server 50. Herein, the measurement data includes the pressure measurement value measured by the air mattress 10, a pressure change amount, the sleep time, and a pressure adjustment amount for each section.

The mattress memory unit 17 stores the set value or the user information received by the mattress communication unit 16. In addition, the mattress memory unit stores the measurement data measured and calculated by the pressure sensor unit 14, the sleep time measuring unit 18, the pressure change amount calculating unit 19, and the pressure adjustment amount calculating unit 20.

The sleep time measuring unit 18 measures the sleep time based on the time that a user uses the air mattress 10. The time from a moment when a user turns on the air mattress 10 to a moment when a user turns off the air mattress 10 is measured. For example, the set time received from the user terminal 30 is measured as the sleep time.

Furthermore, the sleep time measuring unit 18 has a timer function. The sleep time measuring unit has an automatic termination function or an alarm function according to the sleep time set by a user as the set value, etc. For example, after the time set by a user, a function such as a pressure adjusting function, a pressure measuring function, etc. of the air pockets 110 of the air mattress 10 is automatically terminated.

Furthermore, the sleep time measuring unit 18 measures the time that a user uses the air mattress 10 based on pressure applied to the air pocket unit 11, even when a user does not set the sleep time. For example, the time during which the load of a user is applied to the air pocket unit 11 is measured as a use time.

The pressure change amount calculating unit 19 calculates the pressure change amount of the air pocket unit 11 while a user uses the air mattress 10. Specifically, the pressure change amount calculating unit 19 calculates the pressure change amount of the air pocket unit 11 during the sleep time based on the pressure measurement value measured in real time by the pressure sensor unit 14.

For example, the pressure change amount may be a difference between an initial pressure measurement value that is initially set by the set value or the user information and a change pressure measurement value at which the pressure of the air pockets 110 is changed.

Specifically, when the pressure change amount calculating unit 19 calculates the pressure change amount at intervals of one hour, the pressure change amount calculated by the pressure change amount calculating unit 19 may be the difference between the initial pressure measurement value and the change pressure measurement value. For example, the pressure change amount at time T2 is obtained by subtracting the initial pressure measurement value from the change pressure measurement value at time T2. Likewise, the pressure change amount at time T3 is obtained by subtracting the initial pressure measurement value from the change pressure measurement value at time T3.

Alternatively, the pressure change amount may be obtained by a difference between change pressure measurement values that change at intervals of one hour. For example, the pressure change amount up to time T2, one hour after time T1, is calculated by subtracting the pressure measurement value at time T1 from the pressure measurement value at time T2.

The pressure adjustment amount calculating unit 20 calculates the pressure adjustment amount for adjusting the pressure of the air pocket unit 11 to be within an optimum air pocket pressure range according to the user based on the calculated pressure change amount. For example, the pressure adjustment amount calculating unit 20 calculates the pressure adjustment amount for each section that allows a user to feel comfortable based on the sleep posture thereof.

Herein, the optimum air pocket pressure range may range from a preset lower limit value of pressure to a preset upper limit value of pressure that are determined based on the set value and the user information.

In a section of the multiple sections where the pressure change amount is equal to or greater than the preset upper limit value, the pressure adjustment amount calculating unit 20 calculates the pressure adjustment amount such that the pressure of the air pockets 110 in the corresponding section is less than the preset upper limit value. In addition, in a section of the multiple sections where the pressure change amount is equal to or less than the preset lower limit value, the pressure adjustment amount calculating unit calculates the pressure adjustment amount such that the pressure of the air pockets 110 in the corresponding section is greater than the preset lower limit value.

Thus, the mattress controller 13 adjusts air in the air pockets 110 based on the pressure adjustment amount calculated by the pressure adjustment amount calculating unit 20.

Specifically, the mattress controller 13 controls to allow air in the air pockets 110 to be discharged in the section of the multiple sections where the pressure change amount is equal to or greater than the preset upper limit value, based on the pressure adjustment amount calculated by the pressure adjustment amount calculating unit 20. In addition, the mattress controller controls to allow air to be supplied to the air pockets 110 in the section of the multiple sections where the pressure change amount is equal to or less than the preset lower limit value, based on the pressure adjustment amount calculated by the pressure adjustment amount calculating unit 20.

For example, depending on a posture of a user, there may be a difference in pressure applied to each section of the air mattress 10. For example, when the load of a user is concentrated in the third section 11-3 and the pressure of the third section 11-3 is higher than the preset upper limit value, air in the air pockets 110 in the corresponding section is allowed to be discharged to be less than the preset upper limit value.

The custom pressure calculating unit 21 measures the user's load for each section based on the initial pressure measurement value measured by the pressure sensor unit 14 when a user lies on the air mattress 10. The pressure adjustment amount according to a user is calculated based on the user information or the measured load for each section. For example, when a user lies on the mattress, it is measured which section receives a relatively large load and which section receives a relatively small load, based on the initial pressure measurement value, whereby the pressure of the air pockets 110 for each section according to the user's body is obtained. Thus, it is possible to adjust the pressure of the air pockets 110 depending on the user's body.

The microphone 22 and the snoring determination unit 23 determine whether a user is snoring.

The microphone 22 measures noise around the air mattress 10 during the use time of the air mattress 10.

When the noise is detected by the microphone 22, the snoring determination unit 23 checks an average change amount of the pressure change amount of the air pockets 110 of the air mattress 10 during a preset time range T4, based on a noise detection time T3 that the noise is detected, to determine whether a user is snoring.

Specifically, when the noise is detected by the microphone 22, the snoring determination unit 23 recognizes that a user is snoring when the average change amount of the pressure change amount calculated during the preset time range T4 from the noise detection point T3 is within a preset range D, and recognizes that the noise is an external noise when the average change amount of the pressure change amount is less than or greater than the preset range D.

FIG. 12 is a block diagram schematically showing a configuration of a server according to the embodiment of the present invention.

Referring to FIG. 12, the server 50 includes a server controller 51, a server communication unit 52, a server memory unit 53, a sleep pattern analyzing unit 54, and a sleep quality analyzing unit 55.

The server 50 receives the measurement data from the air mattress 10, analyzes the sleep pattern and the sleep quality of a user, and transmits a result of analysis to the user terminal 30.

The server controller 51 controls the server communication unit 52, the server memory unit 53, the sleep pattern analyzing unit 54, and the sleep quality analyzing unit 55 to control the server 50.

The server communication unit 52 communicates with the air mattress 10 and the user terminal 30. Specifically, the server communication unit receives the measurement data from the air mattress 10 and transmits information of the analyzed sleep pattern and sleep quality to the user terminal 30.

The server memory unit 53 stores the measurement data, the sleep pattern information, and the sleep quality information for each user.

The sleep pattern analyzing unit 54 analyzes the sleep time and the sleep posture based on the measurement data. Specifically, the sleep pattern analyzing unit analyzes the sleep time by calculating a daily sleep time, a weekly average sleep time, and a monthly average sleep time based on sleep time data received from the sleep time measuring unit 18.

In addition, the sleep pattern analyzing unit 54 determines and analyzes the sleep posture of a user by measuring, by the pressure sensor unit 14, the pressure in each section where the pressure increases. For example, it is determined that a user lies on his or her side when the pressure change amount of the first section 11-1 is greater than the pressure change amount of other sections. When a user lies on his or her side, a relatively large load is applied to the first section 11-1 where the user's shoulder is located and a relatively small load is applied to the second section 11-2 where the user's waist is located.

Furthermore, it is determined that a user lies on his or her back when the pressure change amount of the third section 11-3 is greater than the pressure change amount of other sections. When the load is entirely applied to the third section 11-3 where the user's buttocks are located, it is determined that a user lies on his or her back.

In addition, the load is concentrated in a specific section such as when the load is concentrated in the first section 11-1 and the second section 11-2, or when the load is concentrated in the second section 11-2 and the third section 11-3, it is determined that a user curls up on his or her side in a fetal posture.

As described above, the posture of a user is ascertained based on load distribution for each section. Thus, the sleep pattern analyzing unit 54 analyzes a main sleep posture taken by a user during the sleep time, and time per sleep posture.

Specifically, during the user's sleep time, the user's sleep posture including a side posture, a back posture, a stomach posture, a fetal posture, etc. is ascertained due to a pressure change of the air pockets 110. In addition, a maintaining time of each posture is ascertained to analyze the main sleep posture mainly taken by a user during the sleep time, and the time per sleep posture.

The sleep quality analyzing unit 55 divides a sleep state of a user into a deep sleep state, a light sleep state, and a wake state, and determines and analyzes the sleep state based on the measurement data, thereby scoring the sleep quality.

The sleep quality analyzing unit 55 determines that a user is in the deep sleep (NREM sleep: non-rapid eye movement sleep) state when the average change amount (i.e., an average change rate) of the pressure change amount of the entire section of the air pockets 110 is within a preset range A. Furthermore, the sleep quality analyzing unit determines that a user is in the light sleep (REM sleep: rapid eye movement sleep) state when the average change amount of the pressure change amount of the entire section of the air pocket unit 11 is within a preset range B. Furthermore, the sleep quality analyzing unit determines that a user is in the wake state when the average change amount of the pressure change amount of the entire section of the air pocket unit 11 is within a preset range C.

In other words, the sleep quality analyzing unit assigns a score to each of the ranges A, B, and C according to the average change amount of the pressure change amount of the entire section of the air pocket unit 11, and calculates an average value based on the sleep time to score the sleep quality of a user. Specifically, a score a is assigned to the preset range A, a score b is assigned to the preset range B, and a score c is assigned to the preset range C.

For example, the sleep quality analyzing unit 55 determines the deep sleep state when the average change amount of pressure is equal to or less than 10%, determines the light sleep state when the average change amount of pressure is greater than 10% and equal to or less than 30%, and determines the wake state when the average change amount of pressure is greater than 30%. In the case of the deep sleep state ten scores are assigned. In the case of the light sleep state, five scores are assigned. In the case of the wake state, one score is assigned. In this manner, a score is assigned to each state, the sum of the score of each state according to time is calculated, and the sum is divided by a total time, thus calculating a sleep quality score.

FIG. 13 shows a process of scoring the sleep quality according to the embodiment of the present invention, FIG. 13a is a graph showing a pressure change rate as a function of time in order to score the sleep quality according to the embodiment of the present invention, and FIG. 13b is a view showing a formula for scoring the sleep quality according to FIG. 13a.

Referring to FIGS. 13a and 13b, the sleep quality analyzing unit 55 represents the average change amount of the pressure change amount of the entire section of the air pocket unit 11 measured by a pressure change rate measuring unit 19 over time. For example, the average change amount of pressure is represented at intervals of one hour.

FIG. 13a shows a graph showing the pressure change rate of the air pocket unit 11 measured during the sleep time, for example, from twelve a.m. to nine a.m., as an example of the user's sleep time.

It is seen that the average change amount of pressure from a twelve o'clock a user started sleeping to two o'clock is greater than the preset range C, so that it is determined that a user is in the wake state.

It is seen that the average change amount of pressure between two o'clock and three o'clock is within the preset range B, so that it is determined that a user is in the light sleep state.

Thereafter, it is shown that the average change amount of pressure between three o'clock and seven o'clock is equal to or less than the preset range A, so that it is determined that a user is in the deep sleep state.

It is seen that the average change amount of pressure between seven o'clock and nine o'clock gradually increases from the preset ranges B to C, so that it is determined that a user gradually wakes up from sleeping.

In summary, a time zone where the average change amount of pressure is measured as the preset range A is from three to seven o'clock, which indicates four hours in a total time. A time zone where the average change amount of pressure is measured as the preset range B is from one to three o'clock and from seven to eight o'clock, which indicates three hours in a total time. A time zone where the average change amount of pressure is measured as the preset range C is from twelve to one o'clock and from eight to nine o'clock, which indicates two hours in a total time.

The scores a, b, and c are respectively assigned to the preset ranges A, B, and C, thus scoring the sleep quality. In the case of the deep sleep state, a high score is assigned, in the case of the wake state, a low score is assigned, and in the case of the light sleep state, a medium score is assigned.

FIG. 13b shows that the sleep quality is scored using the scores assigned to the preset ranges.

Referring to FIG. 13b, an average score of the sleep quality is obtained by multiplying the scores corresponding to each sleep state and the time during which each sleep state is maintained, and a result of multiplication is divided by the total time.

For example, the score a of the deep sleep state measured within the preset range A is multiplied by four hours of a deep sleep time, the score b of the deep sleep state measured within the preset range B is multiplied by three hours of the deep sleep time, and the score c of the deep sleep state measured within the preset range c is multiplied by two hours of the deep sleep time. Thereafter, the sum of multiplication results is divided by nine hours of a total sleep time, thereby calculating the average score.

The preset range A is assigned with ten scores, the preset range B is assigned with five scores, and the preset range C is assigned with one score. In this case, referring to FIG. 13b, the sleep quality is scored by dividing the sum of (ten×five), (five×three), and (one×two) by nine that is the total sleep time.

FIG. 14a is a view showing a setting screen of a user terminal according to the embodiment of the present invention, FIG. 14b is a view showing a sleep quality score screen of the user terminal according to the embodiment of the present invention, and FIG. 14c is a view showing a sleep pattern analysis screen of the user terminal according to the embodiment of the present invention.

Referring to FIG. 14a, a user manually adjusts the pressure of the mattress using a pressure adjustment menu x1. However, FIG. 14a shows that, by way of example, a user manually adjusts the pressure using the pressure adjustment menu x1, but the present invention is not limited thereto. As described above, the pressure of the mattress is automatically adjusted by configurations including the mattress controller 13, the pressure adjustment amount calculating unit 20, etc.

The setting of the first air pocket unit 11L disposed at the left side and the second air pocket unit 11R disposed at the right side is switched using an L/R switching menu x2.

Using a time setting menu x3, a user sets the use time of the air mattress 10, that is, the sleep time. However, the present invention is not limited to the case where the sleep time is set by a user, and the time setting is performed automatically based on the user's use time of the air mattress 10.

Using a user information input menu x4, a user inputs the body condition of a user, including the height, the weight, etc.

Referring to FIG. 14b, the smart mattress system 1 enabling alarm control provides the scored sleep quality to a user using the user terminal 30. The total score is displayed such that a user ascertains his or her sleep quality, and a graph of the sleep state of a user as a function of time is displayed. In addition, the total sleep time, the sleep time of the deep sleep state, the sleep time of the light sleep state, and the sleep time of the wake state are displayed.

Referring to FIG. 14c, there is shown a screen on which the sleep pattern provided to a user by the smart mattress system 1 enabling alarm control is displayed using the user terminal 30. The total sleep time and the time per sleep posture are displayed, such that a user ascertains his or her sleep pattern. For example, the time according to the user's posture such as the back posture, the side posture, the fetal posture, etc. is displayed. Based on this, the user's posture that has been maintained for most of the time is displayed as the main sleep posture.

FIG. 15 is a perspective view showing the air pillow according to the embodiment of the present invention, and FIG. 16 is a block diagram showing a configuration of the air pillow according to the embodiment of the present invention.

Referring to FIGS. 15 and 16, the air pillow 70 includes a cover 71, an air cell 72, a pillow valve 73, an air supply unit 74, a pillow pressure sensor unit 75, a pillow communication unit 76, and a pillow controller 77.

The cover 71 forms an appearance of the air pillow 70.

The air cell 72 is disposed inside the cover 71. The air cell 72 has a hollow portion formed therein and is configured to inflate due to air inflow or to deflate due to air outflow.

The air cell 72 includes a first air cell 72a and a second air cell 72b. In the present embodiment, two air cells 72 are provided, but are not limited thereto. One air cell 72 may be provided and multiple air cells 72 may be provided.

As an example, the first air cell 72a is located under a head of a user and the second air cell 72b is located under a neck of a user. Thus, the heights of the first and second air cells located under the neck and the head of a user are individually adjusted. In other words, the first air cell 72a is located in an upper ⅔ portion of the pillow 70, and the second air cell 72b is located in a lower ⅓ portion thereof.

The first air cell 72a and the second air cell 72b are connected with a first nozzle 721 and a second nozzle 722, respectively. The first nozzle 721 may be an inlet to allow air supply to the first air cell 72a and air discharge from the first air cell 72a. Likewise, the second nozzle 722 may be an inlet to allow air supply to the second air cell 72b and air discharge from the second air cell 72b.

The first nozzle 721 and the second nozzle 722 are respectively provided at the first air cell 72a and the second air cell 72b, whereby the pressure of the first air cell 72a and the pressure of the second air cell 72b are adjusted individually. Although the first nozzle 721 and the second nozzle 722 are provided in the present embodiment, the present invention is not limited thereto. The nozzle may be provided at each air cell 72 to correspond to the number of air cells 72.

The pillow valve 73 adjusts air supply from the air supply unit 74 and air discharge from the air cell 72. The valve 73 may be a solenoid valve. However, the present invention is not limited thereto and may include various types of valves 73.

The air supply unit 74 allows air to be supplied to the air cell 72. Specifically, air is supplied into the hollow portion of the air cell 72. For example, the air supply unit 74 may be comprised of a pump for supplying air. The air supply unit 74 is provided in the cover 71. The air supply unit 74 allows air to be supplied into the air cell 72 through a first supply line 741 and a second supply line 742.

The first supply line 741 allows the first nozzle 721 of the first air cell 72a and the pillow valve 73 to communicate with each other, and the second supply line 742 allows the second nozzle 722 of the second air cell 72b and the pillow valve 73 to communicate with each other. In other words, when the pillow valve 73 is opened, air supplied from the air supply unit 74 is supplied to the first air cell 72a through the first supply line 741. In addition, air supplied from the air supply unit 74 is supplied to the second air cell 72b through the second supply line 742.

The pillow pressure sensor unit 75 measures the pressure of the air cell 72. The pillow pressure sensor unit 75 measures the pressure of the air cell 72 and individually measures the pressure of the first air cell 72a and the pressure of the second air cell 72b. The pillow pressure sensor unit 75 is provided in the pillow valve 73. For example, one pillow pressure sensor unit 75 is connected to the first supply line 741 and the second supply line 742 in the pillow valve 73 to individually measure the pressures of the first supply line 741 and the second supply line 742. Accordingly, the pillow pressure sensor unit 75 individually measures the pressure of the first air cell 72a and the pressure of the second air cell 72b.

The pillow communication unit 76 communicates with the mattress communication unit 16 of the air mattress 10, the user terminal 30, and the server 50 to transmit and receive data. Specifically, the pillow communication unit 76 receives the set value or the user information from the user terminal 30. In addition, the pillow communication unit 76 receives the user's sleep posture according to the pressure measurement value measured by the air mattress 10 from the mattress communication unit 16.

The pillow controller 77 is disposed inside the cover 71 to adjust the pressure of the air cell 72. The pillow controller 77 adjusts the pressure of the air cell 72 based on an initial set value received from the user terminal 30. In addition, the pillow controller 77 controls the air supply unit 74 and the pillow valve 73 based on the user's sleep posture received from the mattress communication unit 16 to adjust the pressure of the air cell 72. For example, when it is determined that the pressure change amount of the third section 11-3 where the user's buttocks are located is greater than the pressure change amount of other sections and thus it is determined that a user lies on his or her back, the pressure change amount being measured by the air mattress 10. When a user lies on his or her back, the height of the second air cell 72b located under the neck of a user is adjusted to increase, thereby allowing a user to maintain a comfortable sleep posture. Thus, when it is determined that a user lies on his or her back based on the measured pressure measurement value received from the mattress communication unit 16 of the air mattress 10, the pillow controller 77 allows air to be supplied to the second air cell 72b to increase the pressure of the second air cell 72b.

Conversely, when it is determined that the pressure change amount of the first section 11-1 measured by the air mattress 10 is greater than the pressure change amount of other sections and thus it is determined that a user lies on his or her side, the pillow controller 77 allows air to be supplied to the first air cell 72a located under the head of a user to increase the pressure of the first air cell 72a.

Thus, it is possible to adjust the pressure of the air pillow 70 depending on the sleep posture of a user, thereby providing a comfortable sleep to a user.

FIG. 17 is a plan view showing an air pillow according to another embodiment of the present invention.

Referring to FIG. 17, an air pillow 70 includes multiple air cells 72.

Specifically, a first air cell 72a includes a first-first air cell 72a-1 to a first-tenth air cell 72a-10. In other words, multiple air cells 72a-1, 72a-2, . . . , and 72a-n are arranged under the head of a user and communicate with each other.

Likewise, a second air cell 72b includes a second-first air cell 72b-1 to a second-five air cell 72b-5. In other words, multiple air cells 72b-1, 72b-2, . . . , and 72b-n are arranged under the neck of a user and communicate with each other.

FIGS. 18 to 22 are flowcharts showing a method of operating the smart mattress system enabling alarm control according to the embodiment of the present invention.

Referring to FIGS. 18 to 22, the smart mattress system 1 enabling alarm control is started from a set value information receiving step S100 of receiving, by the air mattress 10 and the air pillow 70, the set value including the initial pressure value, an alarm time, etc. or the user information including the user's body information from the user terminal 30.

There is included an initial pressure adjusting step S200 of respectively adjusting, by the mattress controller 13 and the pillow controller 77, the pressure of the air pockets 110 of the air mattress 10 and the pressure of the air cell 72 of the air pillow 70, based on the received set value or user information.

The initial pressure adjusting step S200 includes a mattress initial pressure adjusting step S210 and a pillow initial pressure adjusting step S220.

In the mattress initial pressure adjusting step S210, an initial pressure of the air mattress 10 is adjusted based on the set value or the user information received in the set value information receiving step S100. For example, when a user sets an initial pressure value of the air mattress 10 to 50 pa using the user terminal 30, the pressure of the air mattress 10 is adjusted in the mattress initial pressure adjusting step S210 such that a pressure value corresponds to 50 pa.

On the other hand, a user inputs a pressure adjustment range for setting the firmness of the air mattress 10 to the user terminal 30. For example, the pressure adjustment range may range from 1 to 100 pa. This may be divided into five ranges. A first range that is the lowest pressure range may range from 1 to 20 pa. Sequentially, a second range may range from 21 to 40 pa, a third range may range from 41 to 60 pa, a fourth range may range from 61 to 80 pa, and finally a fifth range may range from 81 to 100 pa. The first range is the lowest pressure range, and thus the firmness of the air mattress 10 is set to be low. Thus, it is possible to realize a soft air mattress 10. Conversely, the fifth range is the highest pressure range, and thus the firmness of the air mattress 10 is set to be high, whereby it is possible to realize a rigid air mattress 10.

In the pillow initial pressure adjusting step 220, as in the mattress initial pressure adjusting step S210, the initial pressure of the air pillow 70 is adjusted based on the set value or the user information received in the set value information receiving step S100.

There is included a pressure measuring step S300 of respectively measuring, by the pressure sensor unit 14 and the pillow pressure sensor unit 75, the pressure of the air pockets 110 and the pressure of the air cell 72 in real time, the pressures of the air pockets and the air cell changing depending on a movement of a user.

The pressure measuring step S300 includes a mattress pressure measuring step S310 and a pillow pressure measuring step S320.

In the mattress pressure measuring step S310, the pressure of the air pockets 110 that changes in real time is measured by the pressure sensor unit 14. Herein, the pressure sensor unit 14 measures the pressure of the air pockets 110 for each section of the air pocket unit 11.

In the pillow pressure measuring step S320, the pressure of the air cell 72 that changes in real time is measured by the pillow pressure sensor unit 75. However, the pillow pressure sensor unit 75 individually measures the pressure of one or more air cells 72 provided in the air pillow 70. For example, when two air cells 72 are provided, the pressure of two air cells 72 is individually measured. In other words, in the pillow pressure measuring step S320, the pressure of the first air cell 72a and the pressure of the second air cell 72b are individually measured in real time by the pillow pressure sensor unit 75.

There is included a pressure change amount calculating step s400 of calculating, by the pressure change amount calculating unit 19, the pressure change amount of the air pockets 110 based on the pressure measurement value measured in real time in the pressure measuring step S300. Specifically, the pressure change amount calculating unit 19 calculates the pressure change amount of the air pockets 110 based on the pressure measurement value of the air pockets 110 of the air mattress 10 that is measured in real time in the mattress pressure measuring step S310.

After the pressure change amount calculating step S400, a sleep posture determining step S410 and a sleep state determining step S420 are performed.

In the sleep posture determining step S410, the sleep posture of a user is determined based on the pressure change amount of the air pockets 110 that is calculated in the pressure change amount calculating step S400. As described above, the air mattress 10 is divided into the multiple sections including the first section 11-1, the second section 11-2, the third section 11-3, and the fourth section 11-4, and the sleep posture of a user is determined based on the pressure change amount of in each section. For example, it is determined that a user lies on his or her side when the pressure change amount of the first section 11-1 is greater than the pressure change amount of other sections, and it is determined that a user lies on his or her back when the pressure change amount of the third section 11-3 is greater than the pressure change amount of other sections.

In the sleep state determining step S420, it is determined whether the sleep state of a user is the deep sleep (NREM sleep) state or the light sleep (REM sleep) state based on the average change amount of the pressure change amount calculated in the pressure change amount calculating step S400.

In the sleep state determining step S420, when the average change amount of the pressure change amount of the air pockets 110 calculated in the pressure change amount calculating step S400 is within the preset range A, the mattress controller 13 determines that a user is in the deep sleep (NREM sleep) state. In addition, when the average change amount of the pressure change amount of the air pockets 110 is within the preset range B, the mattress controller 13 determines that a user is in the light sleep (REM sleep) state.

There is included a pressure adjustment amount calculating step S500 of individually calculating, by the pressure adjustment amount calculating unit 20, the pressure adjustment amount of the air pockets 110 and the pressure adjustment amount of the air cell 72 based on the calculated pressure change amount.

The pressure adjustment amount calculating step S500 includes a mattress pressure adjustment amount calculating step S510 and a pillow pressure adjustment amount calculating step S520.

In the pressure adjustment amount calculating step S500, the pressure adjustment amount is determined based on the sleep posture determined in the sleep posture determining step S410.

In the mattress pressure adjustment amount calculating step S510, the pressure adjustment amount of the air pockets 110 is calculated based on the sleep posture of a user determined in the sleep posture determining step S410.

For example, when it is determined that a user lies on his or her back, the load of a user is concentrated in the third section 11-3 so that the pressure of the third section 11-3 is greater than the preset upper limit value. In this case, the pressure adjustment amount is calculated such that the pressure of the air pockets 110 in the third section 11-3 is less than the preset upper limit value.

In the pillow pressure adjustment amount calculating step S520, the pressure adjustment amount of the air cell 72 is calculated based on the sleep posture of a user determined in the sleep posture determining step S410.

For example, when it is determined that the sleep posture of a user is the side posture, a large load is applied to the first air cell 72a located under the head of a user, and a small load is applied to the second air cell 72b located under the neck of a user. Accordingly, air is allowed to flow into the first air cell 72a located under the head of a user, while air is allowed to be discharged from the second air cell 72b located under the neck of a user. Alternatively, air inflow is performed such that an air inflow amount of the second air cell 72b is reduced than an air inflow amount of the first air cell 72a. Thus, when a user lies on his or her side, the neck of a user is prevented from being pressed against the pillow. In other words, the air inflow amount and the air discharge amount are determined depending on the load applied to the first air cell 72a and the second air cell 72b.

There is provided a pressure adjusting step S600 of individually adjusting the pressure of the air pockets 110 and the pressure of the air cell 72 based on the pressure adjustment amounts calculated by the pressure adjustment amount calculating unit 20.

The pressure adjusting step S600 includes a mattress pressure adjusting step S610 and a pillow pressure adjusting step S620. For example, in the pressure adjusting step S600, pressure adjustment is performed based on the sleep posture determined in the sleep posture determining step S410.

In the mattress pressure adjusting step S610, the pressure of the air pockets 110 is adjusted based on the pressure adjustment amount calculated in the mattress pressure adjustment amount calculating step S510.

In the pillow pressure adjusting step S620, the pressure of the air cell 72 is adjusted based on the pressure adjustment amount calculated in the pillow pressure adjustment amount calculating step S520.

As described above, when it is determined that a user lies on his or her side in the sleep posture determining step S410, the pillow controller 77 of the air pillow 70 allows air to flow into the first air cell 72a located under the head of a user. In addition, when it is determined that a user lies on his or her back in the sleep posture determining step S410, the pillow controller 77 of the air pillow 70 allows air to flow into the second air cell 72b located under the neck of a user.

There is included a sleep information analyzing step S700 of receiving, by the server 50, the measurement data including the pressure measurement value, the pressure change amount, the sleep time, and the pressure adjustment amount for each section from the air mattress 10 to analyze the sleep pattern and the sleep quality of a user.

The sleep information analyzing step S700 includes a sleep pattern analyzing step s710 of analyzing, by the server 50, the sleep posture and the sleep time based on the measurement data received from the air mattress 10.

In the sleep pattern analyzing step S710, the sleep pattern analyzing unit 54 analyzes the sleep posture of a user by measuring, by the pressure sensor unit 14, the pressure in each section where the pressure increases. It is determined that a user lies on his or her side when the pressure change amount of the first section 11-1 is greater than the pressure change amount of other sections. Furthermore, it is determined that a user lies on his or her back when the pressure change amount of the third section 11-3 is greater than the pressure change amount of other sections.

There is included a sleep quality analyzing step S730 of dividing, by the server 50, the sleep state of a user into the deep sleep state, the light sleep state, and the wake state based on the measurement data received from the air mattress 10, determining the sleep state based on the measurement data, and analyzing the sleep quality.

There is included an information providing step S800 of receiving, by the user terminal 30, user's sleep information analyzed by the server 50 to provide the sleep information to a user.

There is included a snoring detecting step S900 of detecting whether a user is snoring during a sleep time of a user.

The snoring detecting step S900 includes a noise detecting step S910, a snoring checking step S920, and a snoring stopping step S930.

In the noise detecting step S910, the noise is detected by the microphone 22.

In the snoring checking step S920, when the noise is detected in the noise detecting step S910, it is checked that the average change amount of the pressure change amount calculated during the preset time range T4 from the noise detection time T3 that the noise is detected is within the preset range D to check whether a user is snoring.

When the average change amount of the pressure change amount is within the preset range D, it is recognized that a user is snoring. When the average change amount of the pressure change amount is less than or greater than the preset range D, it is recognized that the noise is an external noise.

The preset range D may be a range where a user is determined to use a bed and to be sleeping. A minimum value of the preset range D is determined by a minimum load applied when a user uses a bed. A case where the pressure change amount is less than the minimum value of the preset range D may indicate a case where a user does not use the mattress. Accordingly, the sound detected by the microphone 22 when a user does not use the mattress is recognized as an external noise.

A maximum value of the preset range D is determined based on the pressure change amount when a user moves most in sleep. A case where the pressure change amount exceeds the maximum value of the preset range may indicate a case where a user uses the mattress while being awake rather than sleeping. Accordingly, the noise detected by the microphone 22 when the pressure change amount exceeds the preset range D is recognized as an external noise. For example, the sound detected when there is a lot of movement of a user is recognized as an external noise such as a TV sound, a user's conversation sound, etc. rather than a user's snoring sound.

For example, the preset range D includes the preset range A determined to be the deep sleep (NREM sleep) state and the preset range B determined to be the light sleep (REM sleep) state.

In the snoring stopping step S930, when it is determined that a user is snoring in the snoring checking step S920, air inflow and air discharge of the air pockets 110 or the air cell 72 are repeated to apply vibration to a user, thereby allowing a user to transition from the deep sleep (NREM sleep) state to the light sleep (REM sleep) state to stop snoring of a user. For example, in the snoring stopping step S930, when the average change amount of the pressure change amount of the entire section of the air pockets 110 is within the preset range A, it is determined that a user is in the deep sleep (NREM sleep) state. In addition, when the average change amount of the pressure change amount of the entire section of the air pockets 110 is within the preset range B, it is determined that a user is in the light sleep (REM sleep) state.

When a user sets an alarm, there is included an alarm step S1000 of waking a user from sleeping.

The alarm step S1000 includes an alarm setting checking step S1010, a sleep state checking step S1020, a sleep state transitioning step S1030, and an alarm generating step S1040.

In the alarm setting checking step S1010, it is checked whether an alarm is set by a user in the set value information receiving step S100.

In the sleep state checking step S1020, when it is checked that the alarm is set in the alarm setting checking step S1010, it is checked whether the sleep state of a user is the deep sleep (NREM sleep) state or the light sleep (REM sleep) state from the sleep state determining step S420 before a preset alarm time T5 from the alarm time.

In the sleep state transitioning step S1030, when the sleep state of a user checked in the sleep state checking step S1020 is the deep sleep (NREM sleep) state, the pressure of the air pockets 110 or the air cell 82 is adjusted to allow a user to transition from the deep sleep (NREM sleep) state to the light sleep (REM sleep) state before the preset alarm time T5 from the alarm time. Specifically, the sleep state transitioning step S1030 includes a vibration generating step S1031 and a stretch inducing step S1032.

In the vibration generating step S1031, air inflow and air discharge of the air pockets 110 or the air cell 72 are repeated to apply vibration to a user, thereby allowing a user to transition from the deep sleep (NREM sleep) state to the light sleep (REM sleep) state. Specifically, the multiple air pockets 110 simultaneously repeatedly perform air inflow and air discharge or the multiple air cells 72 simultaneously repeatedly perform air inflow and air discharge to generate vibration.

There is included the stretch inducing step S1032 to allow a user to transition from the deep sleep (NREM sleep) state to the light sleep (REM sleep) state. In the stretch inducing step S1032, air inflow and air discharge of the air pockets 110 are performed differently for each section, thereby inducing a user to stretch his/her body. Alternatively, air inflow and air discharge of the multiple air cells are performed differently for each air cell.

In the alarm generating step S1040, the alarm is generated at the alarm time received in the set value information receiving step S100 after a user has transitioned to the light sleep (REM sleep) state.

On the other hand, when it is determined that a user is in the light sleep (REM sleep) state in the sleep state checking step S1020, the alarm generating step S1040 is entered without following the sleep state transitioning step S1030. Accordingly, when it is determined that a user is in the light sleep (REM sleep) state, the alarm is generated at the preset alarm time T5. However, the present invention is not limited thereto, and even when it is determined that a user is in the light sleep (REM sleep) state, the sleep state transitioning step S1030 may be followed by the alarm generating step S1040.

When the pressure measurement value measured by the pressure sensor unit 14 of the air mattress 10 is zero, it is determined that a user has finished using the air mattress 10, and the operation of the smart mattress system 1 enabling alarm control is stopped.

However, when the pressure is continuously measured by the air mattress 10 even after the operation process described above is performed, it is repeated again from the set value information receiving step S100 that is the first step.

While the present invention has been particularly shown and described with reference to exemplary embodiments thereof, it will be understood by those of ordinary skill in the art that various changes and modifications may be made therein without departing from the technical spirit of the present invention. Therefore, the scope of the invention should be determined on the basis of the descriptions in the appended claims, not any specific embodiment, and all equivalents thereof should belong to the scope of the invention.

DESCRIPTION OF THE REFERENCE NUMERALS IN THE DRAWINGS

1: smart mattress system enabling alarm control
10: air mattress
11: air pocket unit
12: body portion
13: mattress controller
14: pressure sensor unit
15: air pump
16: mattress communication unit
17: mattress memory unit
30: server
50: user terminal
100: air pocket module
110: air pocket
130: bottom plate
131: nozzle
140: flow passage
70: air pillow
71: cover
72: air cell
73: pillow valve
74: air supply unit
75: pillow pressure sensor unit
76: pillow communication unit
77: pillow controller

The invention claimed is:

1. A method of operating a smart mattress system enabling alarm control, the system including: an air mattress (10) configured to self-adjust a pressure within the air mattress (10) and to measure the pressure in real time; a user terminal (30) receiving a set value or user information from a user and transmitting the set value or the user information to the air mattress (10); a server (50) receiving measurement data from the air mattress (10) to analyze a sleep pattern and sleep quality of a user and transmitting the analyzed sleep pattern and sleep quality to the user terminal (30); and an air pillow (70) connected with the air mattress (10), the user terminal (30), and the server (50) and configured to self-adjust a pressure within the air pillow (70), the method comprising:

a set value information receiving step (S100) of receiving, by the air mattress (10) and the air pillow (70), the set value including an initial pressure value, an alarm time, or the user information including a body condition of the user from the user terminal (30);

an initial pressure adjusting step (S200) of individually adjusting pressure of an air pocket (110) of the air mattress (10) and pressure of an air cell (72) of the air pillow (70) based on the set value or the user information;

a pressure measuring step (S300) of respectively measuring, by a pressure sensor unit (14) and a pillow pressure sensor unit (75), in real time the pressure of the air pocket (110) and the pressure of the air cell (72) that change depending on a movement of the user;
a pressure change amount calculating step (S400) of calculating, by a pressure change amount calculating unit (19), a pressure change amount of the air pocket (110) based on a pressure measurement value measured in real time;
a pressure adjustment amount calculating step (S500) of individually calculating, by a pressure adjustment amount calculating unit (20), a pressure adjustment amount of the air pocket (110) and a pressure adjustment amount of the air cell (72) based on the calculated pressure change amount;
a pressure adjusting step (S600) of individually adjusting the pressure of the air pocket (110) and the pressure of the air cell (72) based on the pressure adjustment amounts calculated by the pressure adjustment amount calculating unit (20);
an alarm step (S1000) of waking the user from sleeping, wherein the user is allowed to transition from a deep sleep (NREM sleep) state to a light sleep (REM sleep) state before a set alarm time;
a sleep state checking step (S1020) checking whether the sleep state of the user is the deep sleep (NREM sleep) state or the light sleep (REM sleep) state; and
a sleep state transitioning step (S1030) of when the sleep state of the user checked in the sleep state checking step (S1020) is the deep sleep (NREM sleep) state, adjusting the pressure of the air pockets (110) or the air cell (72) to allow the user to transition from the deep sleep (NREM sleep) state to the light sleep (REM sleep) state before a preset alarm time (T5) from the alarm time, wherein the sleep state transitioning step (S1030) includes:
a vibration generating step (S1031) of repeating air inflow and air discharge of the air pockets (110) or the air cell (72) to apply vibration to the user, thereby allowing the user to transition from the deep sleep (NREM sleep) state to the light sleep (REM sleep) state.

2. The method of claim 1, wherein the air mattress (10) includes:
an air pocket unit (11) including multiple air pockets (110) each having a hollow portion formed therein and configured to inflate due to air inflow or to deflate due to air outflow;
a body portion (12) into which the air pocket unit (11) is inserted;
a mattress controller (13) mounted at the body portion (12) and controlling pressure of the air pocket unit (11);
the pressure sensor unit (14) measuring the pressure of the air pocket unit (11) in real time;
an air pump (15) supplying air into the air pockets (110); and
a mattress communication unit (16) communicating with the user terminal (30), the server (50), and the air pillow (70).

3. The method of claim 2, wherein the air mattress (10) includes:
a sleep time measuring unit (18) measuring the sleep time based on a time that the user uses the air mattress (10);
the pressure change amount calculating unit (19) calculating the pressure change amount of the air pocket unit (11) based on the pressure measurement value measured in real time by the pressure sensor unit (14) during the sleep time of the user; and
the pressure adjustment amount calculating unit (20) calculating the pressure adjustment amount based on the calculated pressure change amount such that the pressure of the air pocket unit (11) is within an optimum air pocket pressure range ranging from a preset lower limit value (L) to a preset upper limit value (H) that are determined based on the set value and the user information.

4. The method of claim 3, wherein the air pillow (70) includes:
a cover (71) forming an appearance of the air pillow (70);
an air cell (72) disposed inside the cover (71) and having a hollow portion formed therein, the air cell being configured to inflate air inflow or to deflate due to air outflow;
a pillow valve (73) adjusting air supply to the air cell (72) or air discharge from the air cell (72);
an air supply unit (74) supplying air to the air cell (72);
the pillow pressure sensor unit (75) measuring the pressure of the air cell (72);
a pillow communication unit (76) communicating with the air mattress (10), the user terminal (30), and the server (50); and
a pillow controller (77) disposed inside the cover (71) and adjusting the pressure of the air cell (72).

5. The method of claim 4, wherein the initial pressure adjusting step (S200) includes:
a mattress initial pressure adjusting step (S210) of adjusting an initial pressure of the air pockets (110) based on the set value or the user information received in the set value information receiving step (S100); and
a pillow initial pressure adjusting step (S220) of adjusting an initial pressure of the air cell (72) based on the set value or the user information received in the set value information receiving step (S100).

6. The method of claim 5, wherein the pressure measuring step (S300) includes:
a mattress pressure measuring step (S310) of measuring the pressure of the air pockets (110) that changes in real time; and
a pillow pressure measuring step (S320) of measuring the pressure of the air cell (72) that changes in real time.

7. The method of claim 6, further comprising:
after the pressure change amount calculating step (S400),
a sleep posture determining step (S410) of determining a sleep posture of the user based on the pressure change amount calculated in the pressure change amount calculating step (S400); and
a sleep state determining step (S420) of determining whether a sleep state of the user is the deep sleep (NREM sleep) state or the light sleep (REM sleep) state based on an average change amount of the pressure change amount calculated in the pressure change amount calculating step (S400).

8. The method of claim 7, wherein the air mattress (10) is configured such that the air pockets (110) arranged in multiple rows and multiple columns are divided into multiple sections, and the pressure sensor unit (14) measures the pressure of the air pockets (110) for each section of the multiple sections.

9. The method of claim 8, wherein the alarm step (S1000) includes:
an alarm setting checking step (S1010) of checking whether an alarm is set by the user in the set value information receiving step (S100); and
an alarm generating step (S1040) of generating an alarm at the alarm time received in the set value information receiving step (S100) after the user has transitioned to the light sleep (REM sleep) state.

10. The method of claim 9,
wherein the multiple air pockets (110) by the vibration generating step (S1031) simultaneously repeatedly perform air inflow and air discharge or multiple air cells (72) simultaneously repeatedly perform air inflow and air discharge to generate the vibration.

11. The method of claim 10, wherein the sleep state transitioning step (S1030) further includes:
a stretch inducing step (S1032) of allowing air inflow and air discharge of the air pockets (110) to be performed differently for each section or allowing air inflow and air discharge of the multiple air cells (72) to be performed differently for each cell, thereby inducing a user to stretch his or her body.

12. The method of claim 11, further comprising:
a sleep information analyzing step (S700) of receiving, by the server (50), the measurement data including the pressure measurement value, the pressure change amount, the sleep time, and the pressure adjustment amount for each section from the air mattress (10) to analyze the sleep pattern and the sleep quality of the user; and
an information providing step (S800) of receiving, by the user terminal (30), user's sleep information analyzed by the server (50) to provide the sleep information to the user.

13. The method of claim 12, wherein the server (50) includes:
a server controller (51) controlling the server (50);
a server communication unit (52) communicating with the air mattress (10), the user terminal (30), and the air pillow (70);
a server memory unit (53) storing data received from the air mattress (10), the user terminal (30), and the air pillow (70) and data transmitted to the air mattress (10), the user terminal (30), and the air pillow (70);
a sleep pattern analyzing unit (54) receiving the measurement data including the pressure measurement value, the pressure change amount, the sleep time, and the pressure adjustment amount for each section from the air mattress (10) and analyzing the sleep time and the sleep posture based on the measurement data; and
a sleep quality analyzing unit (55) receiving the measurement data including the pressure measurement value, the pressure change amount, the sleep time, and the pressure adjustment amount for each section from the air mattress (10), classifying the sleep state of the user into the deep sleep (NREM sleep) state, the light sleep (REM sleep) state, and a wake state, determining the sleep state based on the measurement data, and scoring the sleep quality.

14. The method of claim 13, wherein the sleep information analyzing step (S700) includes:
a sleep pattern analyzing step (S710) of analyzing, by the server (50), a sleep posture and the sleep time based on the measurement data received from the air mattress (10).

15. The method of claim 14, wherein the sleep information analyzing step (S700) includes:
a sleep quality analyzing step (S730) of dividing, by the server (50), the sleep state of the user into the deep sleep state, the light sleep state, and the wake state based on the measurement data received from the air mattress (10), determining the sleep state based on the measurement data, and analyzing the sleep quality.

* * * * *